(12) United States Patent
Barta et al.

(10) Patent No.: US 7,250,433 B2
(45) Date of Patent: Jul. 31, 2007

(54) TETRAZOLE AND OXADIAZOLONE SUBSTITUTED β-AMINO ACID DERIVATIVES

(75) Inventors: Nancy Sue Barta, Brighton, MI (US); Norman Lloyd Colbry, Gregory, MI (US); Raymond Hudack, Jr., Grand Blanc, MI (US); Kristin Knapp Lin, Ann Arbor, MI (US); Jacob Bradley Schwarz, Ann Arbor, MI (US); Andrew John Thorpe, Whitmore Lake, MI (US); David Juergen Wustrow, Ann Arbor, MI (US); Zhijian Zhu, Farmington Hills, MI (US)

(73) Assignee: Warner Lambert Company LLC, New York, NY (US)

( * ) Notice: Subject to any disclaimer, the term of this patent is extended or adjusted under 35 U.S.C. 154(b) by 177 days.

(21) Appl. No.: 10/795,760

(22) Filed: Mar. 8, 2004

(65) Prior Publication Data
US 2005/0014804 A1    Jan. 20, 2005

Related U.S. Application Data

(60) Provisional application No. 60/452,871, filed on Mar. 7, 2003.

(51) Int. Cl.
A61K 31/41 (2006.01)
C07D 257/04 (2006.01)

(52) U.S. Cl. ...................... 514/381; 548/250
(58) Field of Classification Search ................ 514/381; 548/250
See application file for complete search history.

(56) References Cited

U.S. PATENT DOCUMENTS

| 4,024,175 A | 5/1977 | Satzinger et al. |
|---|---|---|
| 4,087,544 A | 5/1978 | Satzinger et al. |
| 5,563,175 A | 10/1996 | Silverman et al. |
| 6,316,638 B1 | 11/2001 | Bryans et al. |
| 2003/0176504 A1 | 9/2003 | Dooley et al. |

FOREIGN PATENT DOCUMENTS

| WO | WO 99/08671 | 2/1999 |
|---|---|---|
| WO | WO 99/31057 | 6/1999 |
| WO | WO 99/31074 | 6/1999 |
| WO | WO 99/31075 | 6/1999 |
| WO | WO 99/61424 | 12/1999 |
| WO | WO 00/15611 | 3/2000 |

OTHER PUBLICATIONS

C. Ainsworth, 5-β-aminoethyltetrazole, J.A.C.S., vol. 75, pp. 5728-5729 (1953).*
Sluka et al., Muscle & Nerve, vol. 24, pp. 37-46, 2001 and Vogel et al., Psychopharmacologia, vol. 21, pp. 1-7, 1971.*
Leonard et al., "Centrall Active 2-(Substituted phenyl)-β-alanines," J. Org. Chem., 1961, vol. 26, pp. 4062-4065.*
See Patani et al., "Bioisosterism: A Rational Approach in Drug Design," Chem. Rev. 1996, vol. 96, pp. 3147-3176.*
C. Ainsworth, (J.A.C.S., vol. 75, pp. 5728-5729 (1953)).*
Sluka et al., Muscle & Nerve, vol. 24, pp. 37-46, 2001.*
Vogel et al., Psychopharmacologia, vol. 21, pp. 1-7, 1971.*
Vogel, J.R., et al., "A Simple and Reliable Conflict Proceedure for Testing Anti-Anxiety Agents", Psychopharmacologia, (1971), pp. 1-7, vol. 21.
Berge S.M., et al., "Pharamaceutical Salts", J. of Pharma Sci, (1977), pp. 1-19, vol. 66:1.
Palomino E., Delivery of Drugs Through Dihydropyridine Carriers, Drugs of the Future, (1990), pp. 361-368, vol. 15(4).

(Continued)

Primary Examiner—Joseph K. McKane
Assistant Examiner—Susannah L. Chung
(74) Attorney, Agent, or Firm—Karen DeBenedictis; Suzanne M. Harvey; Charles W. Ashbrook

(57) ABSTRACT

This invention relates to novel tetrazole and oxadiazolone β-amino acids derivatives of the formula

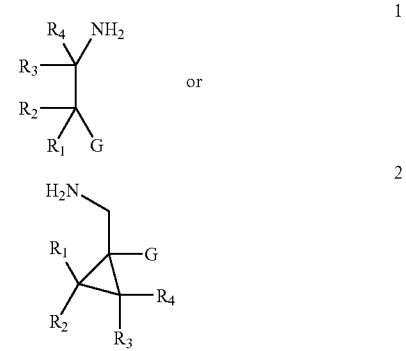

wherein G is

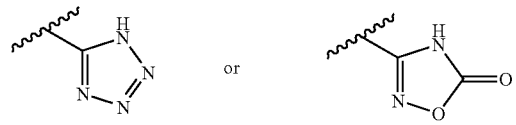

wherein $R^1$ through $R^4$ are defined as in the specification, pharmaceutical compositions containing them and their use for the treatment of various central nervous system and other disorders. The cyclopropyl β-amino acids derivatives of this invention exhibit activity as alpha2delta ligands (α2δ ligands). Such compounds have affinity for the α2δ subunit of a calcium channel.

7 Claims, No Drawings

OTHER PUBLICATIONS

Gee, N.S., et al., The Novel Anticonvulsant Drug, Gabapentin (Neurontin), Binds to the a2d Subunit of a Calcium Channel, J. Biol. Chem., (1996) pp. 5768-5776, vol. 271(10).

Sluka, K., et al., "Unilateral Intramuscular Injections of Acidic Saline Produce A Bilateral, Long-Lasting Hyperalgesia", Muscle & Nerve, (2001), pp. 37-46, vol 24.

Dixon, W., "Efficient analysis of experimental observations", Ann Rev Pharmacol Toxicol, (1980), pp. 441-462, vol. 20.

Randall, L.O & Selitto, J.J., "A Method For Measurement of Analgesic Activity On Inflamed Tissue", Arch. Int. Pharmacodyn, (1957), pp. 409-419, vol. 4.

McManus, J.M., et al., "Tetrazole Analogs of Amino Acids", J Org Chem, 1959, pp. 1643-1649, vol. 24.

Hargreaves, K, et al., "A New Sensitive Method for Measuring Thermal Nociception in Cutaneous Hyperalgesia", Pain, (1988), pp. 77-88, vol. 32.

* cited by examiner

TETRAZOLE AND OXADIAZOLONE SUBSTITUTED β-AMINO ACID DERIVATIVES

CROSS REFERENCE TO RELATED APPLICATIONS

This application claims benefit of priority from U.S. Provisional Application No. 60/452,871, filed on Mar. 7, 2003.

BACKGROUND OF THE INVENTION

This invention relates to novel tetrazole and oxadiazolone substituted β-amino acids derivatives, pharmaceutical compositions containing them and their use for the treatment of various central nervous system and other disorders. The tetrazole and oxadiazolone substituted β-amino acids derivatives of this invention exhibit activity as alpha2delta ligands (α2δ ligand). Such compounds have affinity for the α2δ subunit of a calcium channel. Such compounds have also been referred to in the literature as gamma-aminobutyric acid (GABA) analogs.

Several alpha2delta ligands are known. Gabapentin, a cyclic alpha2delta ligand, is now commercially available (Neurontin®, Warner-Lambert Company) and extensively used clinically for treatment of epilepsy and neuropathic pain. Such cyclic alpha2delta ligands are described in U.S. Pat. No. 4,024,175, which issued on May 17, 1977, and U.S. Pat. No. 4,087,544, which issued on May 2, 1978. Other series of alpha2delta ligands are described in U.S. Pat. No. 5,563,175, which issued on Oct. 8, 1996, U.S. Pat. No. 6,316,638, which issued on Nov. 13, 2001, U.S. Provisional Patent Application No. 60/353,632, which was filed on Jan. 31, 2002, European Patent Application EP 1112253, which was published on Jul. 4, 2001, PCT Patent Application WO 99/08671, which was published on Feb. 25, 1999, and PCT Patent Application WO 99/61424, which was published on Dec. 2, 1999. These patents and applications are incorporated herein by reference in their entireties.

SUMMARY OF THE INVENTION

This invention relates to tetrazole and oxadiazolone substituted β-amino acids derivatives of the formula I or II

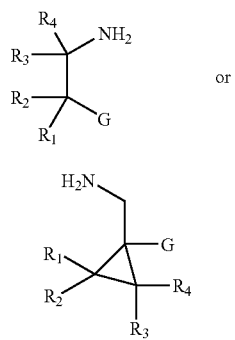

wherein G is

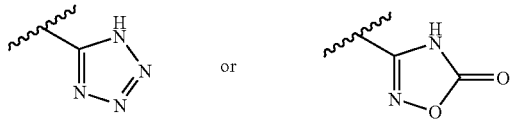

wherein $R^1$ and $R^2$ are selected, independently, from hydrogen, $(C_1-C_{10})$straight or branched alkyl, $(C_2-C_{10})$ straight or branched alkoxyalkyl, phenyl-$(C_{1-3})$straight or branched alkyl and phenyl-$(C_2-C_3)$alkoxyalkyl, wherein said phenyl moieties can optionally be substituted with one or two substituents selected, independently, from halo or $(C_1-C_3)$alkyl;

or $R^1$ and $R^2$, together with the carbon to which they are attached, form a cyclopentyl, cyclohexyl or cycloheptyl ring which can optionally be substituted with one or two substituents selected, independently, from the group of substituents named in the definition of $R^1$ and $R^2$ above; and $R^3$ and $R^4$ are selected, independently, from hydrogen and methyl;

and the pharmaceutically acceptable salts of such compounds.

Preferred embodiments of this invention include the following compounds and their pharmaceutically acceptable salts:

4-Methyl-2-(1H-tetrazol-5-yl)-pentylamine;
3-(1-Aminomethyl-3-methyl-butyl)-4H-[1,2,4]oxadiazol-5-one;
3-Methyl-2-(1H-tetrazol-5-yl)-butylamine;
4-Propyl-2-(1H-tetrazol-5-yl)-heptylamine;
2-Cyclopentyl-2-(1H-tetrazol-5-yl)-ethylamine;
3-(2-Amino-1-cyclopentyl-ethyl)-4H-[1,2,4]oxadiazol-5-one;
4-Methyl-2-(1H-tetrazol-5-yl)-hexylamine;
4-Methyl-2-(1H-tetrazol-5-yl)-hexylamine;
4,4-Dimethyl-2-(1H-tetrazol-5-yl)-hexylamine;
4-Ethyl-2-(1H-tetrazol-5-yl)-hexylamine;
4-Ethyl-2-(1H-tetrazol-5-yl)-octylamine;
4,4-Dimethyl-2-(1H-tetrazol-5-yl)-pentylamine;
5,5-Dimethyl-2-(1H-tetrazol-5-yl)-hexylamine;
2-(1H-Tetrazol-5-yl)-pentylamine;
2-(1H-Tetrazol-5-yl)-octylamine;
4,8-Dimethyl-2-(1H-tetrazol-5-yl)-nonylamine;
5,9-Dimethyl-2-(1H-tetrazol-5-yl)-decylamine;
2-Cyclohexyl-2-(1H-tetrazol-5-yl)-ethylamine;
3-(2-Amino-1-cyclohexyl-ethyl)-4H-[1,2,4]oxadiazol-5-one;
2-(3,5-Dimethyl-cyclohexyl)-2-(1H-tetrazol-5-yl)-ethylamine;
2-Cycloheptyl-2-(1H-tetrazol-5-yl)-ethylamine;
3-(2-Amino-1-cycloheptyl-ethyl)-4H-[1,2,4]oxadiazol-5-one;
3-Cyclohexyl-2-(1H-tetrazol-5-yl)-propylamine;
3,4-Dimethyl-2-(1H-tetrazol-5-yl)-pentylamine;
3-Ethyl-4-methyl-2-(1H-tetrazol-5-yl)-pentylamine;
4-Cyclopentyl-3-methyl-2-(1H-tetrazol-5-yl)-butylamine;
4-Cyclohexyl-3-methyl-2-(1H-tetrazol-5-yl)-butylamine;
3-Phenyl-2-(1H-tetrazol-5-yl)-propylamine;
6-Phenyl-2-(1H-tetrazol-5-yl)-hexylamine;
4-(4-Fluoro-phenyl)-3-methyl-2-(1H-tetrazol-5-yl)-butylamine;
3-Methyl-2-(1H-tetrazol-5-yl)-4-(3-trifluoromethyl-phenyl)-butylamine;
3-Methyl-5-phenyl-2-(1H-tetrazol-5-yl)-pentylamine;
5-(4-tert-Butyl-phenyl)-4-methyl-2-(1H-tetrazol-5-yl)-pentylamine;
2-Methyl-2-(1H-tetrazol-5-yl)-propylamine;
2-Methyl-3-phenyl-2-(1H-tetrazol-5-yl)-propylamine;
3-(2-Amino-1-benzyl-1-methyl-ethyl)-4H-[1,2,4]oxadiazol-5-one;
3-(1-Aminomethyl-spiro[2.3]hex-1-yl)-4H-[1,2,4]oxadiazol-5-one;
C-[1-(1H-Tetrazol-5-yl)-spiro[2.4]hept-1-yl]-methylamine;

3-(1-Aminomethyl-spiro[2.4]hept-1-yl)-4H-[1,2,4]oxadiazol-5-one;
C-[2-Isopropyl-1-(1H-tetrazol-5-yl)-cyclopropyl]-methylamine;
3-(1-Aminomethyl-2-isopropyl-cyclopropyl)-4H-[1,2,4]oxadiazol-5-one;
C-[2-(1-Ethyl-propyl)-1-(1H-tetrazol-5-yl)-cyclopropyl]-methylamine;
3-(1-Aminomethyl-2-isobutyl-cyclopropyl)-4H-[1,2,4]oxadiazol-5-one;
C-[2-Cyclohexyl-1-(1H-tetrazol-5-yl)-cyclopropyl]-methylamine;

Examples of specific embodiments of the present invention are the following compounds and their pharmaceutically acceptable salts:
3-Methyl-1-(1H-tetrazol-5-ylmethyl)-butylamine;
3-(2-Amino-4-methyl-pentyl)-4H-[1,2,4]oxadiazol-5-one;
3-Methyl-1-(1H-tetrazol-5-ylmethyl)-pentylamine;
3-(2-Amino-4-methyl-hexyl)-4H-[1,2,4]oxadiazol-5-one;
3-Methyl-1-(1H-tetrazol-5-ylmethyl)-hexylamine;
3-(2-Amino-4-methyl-heptyl)-4H-[1,2,4]oxadiazol-5-one;
3-Methyl-1-(1H-tetrazol-5-ylmethyl)-heptylamine;
3-(2-Amino-4-methyl-octyl)-4H-[1,2,4]oxadiazol-5-one;
3,3-Dimethyl-1-(1H-tetrazol-5-ylmethyl)-butylamine;
3-(2-Amino-4,4-dimethyl-pentyl)-4H-[1,2,4]oxadiazol-5-one;
3,3-Dimethyl-1-(1H-tetrazol-5-ylmethyl)-pentylamine;
3-(2-Amino-4,4-dimethyl-hexyl)-4H-[1,2,4]oxadiazol-5-one;
3,3-Dimethyl-1-(1H-tetrazol-5-ylmethyl)-hexylamine;
3-(2-Amino-4,4-dimethyl-heptyl)-4H-[1,2,4]oxadiazol-5-one;
3,3-Dimethyl-1-(1H-tetrazol-5-ylmethyl)-heptylamine;
3-(2-Amino-4,4-dimethyl-octyl)-4H-[1,2,4]oxadiazol-5-one;
1-(1-Methyl-cyclopropylmethyl)-2-(1H-tetrazol-5-yl)-ethylamine;
3-[2-Amino-3-(1-methyl-cyclopropyl)-propyl]-4H-[1,2,4]oxadiazol-5-one;
1-(1-Ethyl-cyclopropylmethyl)-2-(1H-tetrazol-5-yl)-ethylamine;
3-[2-Amino-3-(1-ethyl-cyclopropyl)-propyl]-4H-[1,2,4]oxadiazol-5-one;
1-(1-Propyl-cyclopropylmethyl)-2-(1H-tetrazol-5-yl)-ethylamine;
3-[2-Amino-3-(1-propyl-cyclopropyl)-propyl]-4H-[1,2,4]oxadiazol-5-one;
1-(1-Butyl-cyclopropylmethyl)-2-(1H-tetrazol-5-yl)-ethylamine;
3-[2-Amino-3-(1-butyl-cyclopropyl)-propyl]-4H-[1,2,4]oxadiazol-5-one;
3-(1-Aminomethyl-2-methyl-propyl)-4H-[1,2,4]oxadiazol-5-one;
3-Methyl-2-(11 H-tetrazol-5-yl)-pentylamine;
3-(1-Aminomethyl-2-methyl-butyl)-4H-[1,2,4]oxadiazol-5-one;
3-Methyl-2-(1H-tetrazol-5-yl)-hexylamine;
3-(1-Aminomethyl-2-methyl-pentyl)-4H-[1,2,4]oxadiazol-5-one;
3-Methyl-2-(1H-tetrazol-5-yl)-heptylamine;
3-(1-Aminomethyl-2-methyl-hexyl)-4H-[1,2,4]oxadiazol-5-one;
3-(1-Aminomethyl-3-propyl-hexyl)-4H-[1,2,4]oxadiazol-5-one;
3-(1-Aminomethyl-3-methyl-pentyl)-4H-[1,2,4]oxadiazol-5-one;
3-(1-Aminomethyl-3-methyl-pentyl)-4H-[1,2,4]oxadiazol-5-one;
4-Methyl-2-(1H-tetrazol-5-yl)-heptylamine;
3-(1-Aminomethyl-3-methyl-heptyl)-4+[1,2,4]oxadiazol-5-one;
3-(1-Aminomethyl-3,3-dimethyl-pentyl)-4H-[1,2,4]oxadiazol-5-one;
4,4-Dimethyl-2-(1H-tetrazol-5-yl)-heptylamine;
3-(1-Aminomethyl-3,3-dimethyl-hexyl)-4H-[1,2,4]oxadiazol-5-one;
4,4-Dimethyl-2-(1H-tetrazol-5-yl)-octylamine;
3-(1-Aminomethyl-3,3-dimethyl-heptyl)-4H-[1,2,4]oxadiazol-5-one;
3-(1-Ethyl-cyclopropyl)-2-(1H-tetrazol-5-yl)-propylamine;
3-[1-Aminomethyl-2-(1-ethyl-cyclopropyl)-ethyl]-4H-[1,2,4]oxadiazol-5-one;
3-(1-Propyl-cyclopropyl)-2-(1H-tetrazol-5-yl)-propylamine;
3-[1-Aminomethyl-2-(1-propyl-cyclopropyl)-ethyl]-4H-[1,2,4]oxadiazol-5-one;
3-(1-Butyl-cyclopropyl)-2-(1H-tetrazol-5-yl)-propylamine;
3-[1-Aminomethyl-2-(1-butyl-cyclopropyl)-ethyl]-4H-[1,2,4]oxadiazol-5-one;
3-(1-Aminomethyl-3-ethyl-pentyl)-4H-[1,2,4]oxadiazol-5-one;
4-Ethyl-2-(1H-tetrazol-5-yl)-heptylamine;
3-(1-Aminomethyl-3-ethyl-hexyl)-4H-[1,2,4]oxadiazol-5-one;
3-(1-Aminomethyl-3-ethyl-heptyl)-4H-[1,2,4]oxadiazol-5-one;
5-Methyl-2-(1H-tetrazol-5-yl)-hexylamine;
3-(1-Aminomethyl-4-methyl-pentyl)-4H-[1,2,4]oxadiazol-5-one;
3-(1-Aminomethyl-3,3-dimethyl-butyl)-4H-[1,2,4]oxadiazol-5-one;
3-(1-Aminomethyl-4,4-dimethyl-pentyl)-4H-[1,2,4]oxadiazol-5-one;
2-(1H-Tetrazol-5-yl)-propylamine;
3-(1-Aminomethyl-ethyl)-4H-[1,2,4]oxadiazol-5-one;
2-(1H-Tetrazol-5-yl)-butylamine;
3-(1-Aminomethyl-propyl)-4H-[1,2,4]oxadiazol-5-one;
3-(1-Aminomethyl-butyl)-4H-[1,2,4]oxadiazol-5-one;
2-(1H-Tetrazol-5-yl)-hexylamine;
3-(1-Aminomethyl-pentyl)-4H-[1,2,4]oxadiazol-5-one;
2-(1H-Tetrazol-5-yl)-heptylamine;
3-(1-Aminomethyl-hexyl)-4H-[1,2,4]oxadiazol-5-one;
3-(1-Aminomethyl-heptyl)-4H-[1,2,4]oxadiazol-5-one;
3-(1-Aminomethyl-3,7-dimethyl-octyl)-4H-[1,2,4]oxadiazol-5-one;
3-(1-Aminomethyl-4,8-dimethyl-nonyl)-4H-[1,2,4]oxadiazol-5-one;
3-[2-Amino-1-(3,5-dimethyl-cyclohexyl)-ethyl]-4H-[1,2,4]oxadiazol-5-one;
3-(2-Amino-1-cyclohexylmethyl-ethyl)-4H-[1,2,4]oxadiazol-5-one;
4-Cyclohexyl-2-(1H-tetrazol-5-yl)-butylamine;
3-(1-Aminomethyl-3-cyclohexyl-propyl)-4H-[1,2,4]oxadiazol-5-one;
3-(1-Aminomethyl-2,3-dimethyl-butyl)-4H-[1,2,4]oxadiazol-5-one;
3-(1-Aminomethyl-2-ethyl-3-methyl-butyl)-4H-[1,2,4]oxadiazol-5-one;
3-(1-Aminomethyl-3-cyclopentyl-2-methyl-propyl)-4H-[1,2,4]oxadiazol-5-one;
3-(1-Aminomethyl-3-cyclohexyl-2-methyl-propyl)-4H-[1,2,4]oxadiazol-5-one;
2-Phenyl-2-(1H-tetrazol-5-yl)-ethylamine;

3-(2-Amino-1-phenyl-ethyl)-4H-[1,2,4]oxadiazol-5-one;
3-(2-Amino-1-benzyl-ethyl)-4H-[1,2,4]oxadiazol-5-one;
4-Phenyl-2-(1H-tetrazol-5-yl)-butylamine;
3-(1-Aminomethyl-3-phenyl-propyl)-4H-[1,2,4]oxadiazol-5-one;
5-Phenyl-2-(1H-tetrazol-5-yl)-pentylamine;
3-(1-Aminomethyl-4-phenyl-butyl)-4H-[1,2,4]oxadiazol-5-one;
3-(1-Aminomethyl-5-phenyl-pentyl)-4H-[1,2,4]oxadiazol-5-one;
7-Phenyl-2-(1H-tetrazol-5-yl)-heptylamine;
3-(1-Aminomethyl-6-phenyl-hexyl)-4H-[1,2,4]oxadiazol-5-one;
3-Phenyl-2-(1H-tetrazol-5-yl)-butylamine;
3-(1-Aminomethyl-7-phenyl-heptyl)-4H[1,2,4]oxadiazol-5-one;
3-[1-Aminomethyl-3-(4-fluoro-phenyl)-2-methyl-propyl]-4H-[1,2,4]oxadiazol-5-one;
3-(1-Aminomethyl-2-methyl-3-(3-trifluoromethyl-phenyl)-propyl]-4H-[1,2,4]oxadiazol-5-one;
3-(1-Aminomethyl-2-methyl-4-phenyl-butyl)-4H-[1,2,4]oxadiazol-5-one;
3-[1-Aminomethyl-4-(4-tert-butyl-phenyl)-3-methyl-butyl]-4H-[1,2,4]oxadiazol-5-one;
3-(2-Amino-1,1-dimethyl-ethyl)-4H-[1,2,4]oxadiazol-5-one;
2-Benzyl-3-phenyl-2-(1H-tetrazol-5-yl)-propylamine;
3-(2-Amino-1,1-dibenzyl-ethyl)-4H-[1,2,4]oxadiazol-5-one;
2-Methyl-2-(1H-tetrazol-5-yl)-3-(3-trifluoromethyl-phenyl)-propylamine;
3-[2-Amino-1-methyl-1-(3-trifluoromethyl-benzyl)-ethyl]-4H-[1,2,4]oxadiazol-5-one;
3-(3,4-Difluoro-phenyl)-2-methyl-2-(1H-tetrazol-5-yl)-propylamine;
3-[2-Amino-1-(3,4-difluoro-benzyl)-1-methyl-ethyl]-4H-[1,2,4]oxadiazol-5-one;
3-(2,4-bis-Trifluoromethyl-phenyl)-2-methyl-2-(1H-tetrazol-5-yl)-propylamine;
3-[2-Amino-1-(2,4-bis-trifluoromethyl-benzyl)-1-methyl-ethyl]-4H-[1,2,4]oxadiazol-5-one;
C-[1-(1H-Tetrazol-5-yl)-spiro[2.3]hex-1-yl]-methylamine;
C-[1-(1H-Tetrazol-5-yl)-spiro[2.5]oct-1-yl]-methylamine;
3-(1-Aminomethyl-spiro[2.5]oct-1-yl)-4H-[1,2,4]oxadiazol-5-one;
C-[1-(1H-Tetrazol-5-yl)-spiro[2.6]non-1-yl]-methylamine;
3-(1-Aminomethyl-spiro[2.6] non-1-yl)-4H-[1,2,4]oxadiazol-5-one;
C-[1-(1H-Tetrazol-5-yl)-spiro[2.7]dec-1-yl]-methylamine;
3-(1-Aminomethyl-spiro[2.7]dec-1-yl)-4H-[1,2,4]oxadiazol-5-one;
C-[5-Methyl-1-(1H-tetrazol-5-yl)-spiro[2.5]oct-1-yl]-methylamine;
3-(1-Aminomethyl-5-methyl-spiro[2.5]oct-1-yl)-4H-[1,2,4]oxadiazol-5-one;
C-[5,7-Dimethyl-1-(1H-tetrazol-5-yl)-spiro[2.5]oct-1-yl]-methylamine;
3-(1-Aminomethyl-5,7-dimethyl-spiro[2.5]oct-1-yl)-4H-[1,2,4]oxadiazol-5-one;
C-[2,2-Diethyl-1-(1H-tetrazol-5-yl)-cyclopropyl]-methylamine;
3-(1-Aminomethyl-2,2-diethyl-cyclopropyl)-4H-[1,2,4]oxadiazol-5-one;
C-[2,2-Di-n-propyl-1-(1H-tetrazol-5-yl)-cyclopropyl]-methylamine;
3-(1-Aminomethyl-2,2-di-n-propyl-cyclopropyl)-4H-[1,2,4]oxadiazol-5-one;
C-[2-n-Propyl-1-(1H-tetrazol-5-yl)-cyclopropyl]-methylamine;
3-(1-Aminomethyl-2-n-propyl-cyclopropyl)-4H-[1,2,4]oxadiazol-5-one;
3-(1-Aminomethyl-2-(1-ethyl-propyl)-cyclopropyl)-4H-[1,2,4]oxadiazol-5-one;
C-[2-(2-Methyl-butyl)-1-(1H-tetrazol-5-yl)-cyclopropyl]-methylamine;
3-(1-Aminomethyl-2-(2-methyl-butyl)-cyclopropyl)-4H-[1,2,4]oxadiazol-5-one;
C-[2-(2-Methyl-pentyl)-1-(1H-tetrazol-5-yl)-cyclopropyl]-methylamine;
3-(1-Aminomethyl-2-(2-methyl-pentyl)-cyclopropyl)-4H-[1,2,4]oxadiazol-5-one;
C-[2-(2-Methyl-hexyl)-1-(1H-tetrazol-5-yl)-cyclopropyl]-methylamine;
3-(1-Aminomethyl-2-(2-methyl-hexyl)-cyclopropyl)-4H-[1,2,4]oxadiazol-5-one;
C-[2-(2,6-Dimethyl-heptyl)-1-(1H-tetrazol-5-yl)-cyclopropyl]-methylamine;
3-(1-Aminomethyl-2-(2,6-dimethyl-heptyl)-cyclopropyl)-4H-[1,2,4]oxadiazol-5-one;
C-[2-n-Butyl-1-(1H-tetrazol-5-yl)-cyclopropyl]-methylamine;
3-(1-Aminomethyl-2-n-butyl-cyclopropyl)-4H-[1,2,4]oxadiazol-5-one;
C-[2-Isobutyl-1-(1H-tetrazol-5-yl)-cyclopropyl]-methylamine;
C-[2-Cyclopropyl-1-(1H-tetrazol-5-yl)-cyclopropyl]-methylamine;
3-(1-Aminomethyl-2-cyclopropyl-cyclopropyl)-4H-[1,2,4]oxadiazol-5-one;
C-[2-Cyclobutyl-1-(1H-tetrazol-5-yl)-cyclopropyl]-methylamine;
3-(1-Aminomethyl-2-cyclobutyl-cyclopropyl)-4H-[1,2,4]oxadiazol-5-one;
C-[2-Cyclopentyl-1-(1H-tetrazol-5-yl)-cyclopropyl]-methylamine;
3-(1-Aminomethyl-2-cyclopentyl-cyclopropyl)-4H-[1,2,4]oxadiazol-5-one;
3-(1-Aminomethyl-2-cyclohexyl-cyclopropyl)-4H-[1,2,4]oxadiazol-5-one;
C-[2-Cyclopropylmethyl-1-(1 H-tetrazol-5-yl)-cyclopropyl]-methylamine;
3-(1-Aminomethyl-2-cyclopropylmethyl-cyclopropyl)-4H-[1,2,4]oxadiazol-5-one;
C-[2-Cyclobutylmethyl-1-(1H-tetrazol-5-yl)-cyclopropyl]-methylamine;
3-(1-Aminomethyl-2-cyclobutylmethyl-cyclopropyl)-4H-[1,2,4]oxadiazol-5-one;
C-[2-cyclopentylmethyl-1-(1H-tetrazol-5-yl)-cyclopropyl]methylamine;
3-(1-Aminomethyl-2-cyclopentylmethyl-cyclopropyl)-4H-[1,2,4]oxadiazol-5-one;
C-[2-Cyclohexylmethyl-1-(1H-tetrazol-5-yl)-cyclopropyl]-methylamine;
3-(1-Aminomethyl-2-cyclohexylmethyl-cyclopropyl)-4H-[1,2,4]oxadiazol-5-one;
C-[2-Phenyl-1-(1H-tetrazol-5-yl)-cyclopropyl]-methylamine;
3-(1-Aminomethyl-2-phenyl-cyclopropyl)-4H-[1,2,4]oxadiazol-5-one
C-[2-Benzyl-1-(1H-tetrazol-5-yl)-cyclopropyl]-methylamine; and
3-(1-Aminomethyl-2-benzyl-cyclopropyl)-4H-[1,2,4]oxadiazol-5-one.

The phrase "lower alkyl", as used herein, unless otherwise indicated, means a straight or branched alkyl group or radical having from 1 to 6 carbon atoms, and includes methyl, ethyl, n-propyl, i-propyl, n-butyl, i-butyl, sec-butyl, tert-butyl, n-pentyl, n-hexyl, and the like.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "cycloalkyl", unless otherwise stated, means saturated monovalent carbocyclic groups containing from 3 to 8 carbons and are selected from cyclopropyl, cyclobutyl, cyclopentyl, cyclohexyl, cycloheptyl, and cyclooctyl.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

Compounds of the formulas I and II may contain chiral centers and therefore may exist in different enantiomeric and diastereomeric forms. Individual isomers can be obtained by known methods, such as optical resolution, optically selective reaction, or chromatographic separation in the preparation of the final product or its intermediate. This invention relates to all optical isomers and all stereoisomers of compounds of the formula I, both as racemic mixtures and as individual enantiomers and diastereoisomers of such compounds, and mixtures thereof, and to all pharmaceutical compositions and methods of treatment defined above that contain or employ them, respectively. Individual enantiomers of the compounds of formulas I and II may have advantages, as compared with the racemic mixtures of these compounds, in the treatment of various disorders or conditions.

In so far as the compounds of formulas I and II of this invention are basic compounds, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The free base form of the compound may be regenerated by contacting the acid addition salt so formed with a base, and isolating the free base form of the compound in the conventional manner. The free base forms of compounds prepared according to a process of the present invention differ from their respective acid addition salt forms somewhat in certain physical properties such as solubility, crystal structure, hygroscopicity, and the like, but otherwise free base forms of the compounds and their, respective acid addition salt forms are equivalent for purposes of the present invention.

Pharmaceutically acceptable acid addition salts of the basic compounds useful in the method of the present invention include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.,* 1977; 66:1).

In so far as the compounds of formulas I and II of this invention are acidic compounds, they are all capable of forming a wide variety of different salts with various inorganic and organic bases. A pharmaceutically acceptable base addition salt of an acidic compound useful in the method of the present invention may be prepared by contacting the free acid form of the compound with a nontoxic metal cation such as an alkali or alkaline earth metal cation, or an amine, especially an organic amine. Examples of suitable metal cations include sodium cation ($Na^+$), potassium cation ($K^+$), magnesium cation ($Mg^{2+}$); calcium cation ($Ca^{2+}$), and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, supra., 1977). A base addition salt of an acidic compound useful in the method of the present invention may be prepared by contacting the free acid form of the compound with a sufficient amount of a desired base to produce the salt in the conventional manner. The free acid form of the compound may be regenerated by contacting the salt form so formed with an acid, and isolating the free acid of the compound in the conventional manner. The free acid forms of the compounds useful in the method of the present invention differ from their respective salt forms somewhat in certain physical properties such as solubility, crystal structure, hygroscopicity, and the like, but otherwise the salts are equivalent to their respective free acid for purposes of the present invention.

The present invention also includes isotopically labelled compounds, which are identical to those recited in formulas I and II, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances.

Certain of the compounds useful in the method of the present invention can exist in unsolvated forms as well as solvated forms, including hydrated forms. In general, the solvated forms, including hydrated forms, are equivalent to unsolvated forms and are intended to be encompassed within the scope of the present invention.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug that has been chemically modified and may be biologically inactive at its site of action, but which may be degraded or modified by one or more enzymatic or other in vivo processes to the parent bioactive form.

This chemically modified drug, or prodrug, should have a different pharmacokinetic profile than the parent drug, enabling easier absorption across the mucosal epithelium, better salt formulation and/or solubility, improved systemic stability (for an increase in plasma half-life, for example). These chemical modifications may be, for example:

1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means;
2) peptides which may be recognized by specific or non-specific proteinases (A peptide may be coupled to the drug molecule via amide bond formation with the amine or carboxylic acid moiety of the drug molecule by known means);
3) derivatives that accumulate at a site, of action through membrane selection of a prodrug form or modified prodrug form; or
4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug upon hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Prodrugs of compounds of formula I are included within the scope of this invention. Prodrugs and soft drugs are known in the art (Palomino E., *Drugs of the Future*, 1990; 15(4): 361-368). The last two citations are hereby incorporated by reference.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

This invention also relates to a pharmaceutical composition comprising a therapeutically effective amount of a compound of the formula I or II, or a pharmaceutically acceptable salt thereof, and a pharmaceutically acceptable carrier.

This invention also relates to a method of treating a disorder or condition selected from faintness attacks, epilepsy, asphyxia, general anoxia, hypoxia, spinal cord trauma, traumatic brain injury, head trauma, cerebral ischemia, stroke (including thromboembolic stroke, focal ischemia, global ischemia, transient cerebral ishemia attacks and other cerebral vascular problems accompanied by cerebral ischemia such as in patients undergoing carotid endarterectomy or other vascular surgical procedures in general or diagnostic vascular surgical procedures such as angiography), cramp caused by thiosemicarbazide, cardiazole cramp, and cerebral vascular disorders due to acute or chronic cerebrovascular damage such as cerebral infarction, subarachnoid haemorrhage or cerebral oedema in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of neurocardiac disorders such as neurocardiac syncope, neurogenic syncope, hypersensitive Carotid sinus, neurovascular syndrome and arrythmias including arrythmias secondary to gastrointestinal disturbances in a mammal, comprising administering to a mammal in need of such treatment a therapeutically effective amount of a compound of the formula I or II, or a pharmaceutically acceptable salt thereof.

This invention also relates to a method of treating a disorder or condition selected from acute pain, chronic pain, pain resulting from soft tissue and peripheral damage such as acute trauma; postherpetic neuralgia, occipital neuralgia, trigeminal neuralgia, segmental or intercostal neuralgia and other neuralgias; pain associated with osteoarthritis and rheumatoid arthritis; musculo-skeletal pain such as pain associated with strains, sprains and trauma such as broken bones; spinal pain, central nervous system pain such as pain due to spinal cord or brain stem damage; lower back pain, sciatica, dental pain, myofascial pain syndromes, episiotomy pain, gout pain, and pain resulting from burns; deep and visceral pain, such as heart pain; muscle pain, eye pain, inflammatory pain, orofacial pain, for example, odontalgia; abdominal pain, and gynecological pain, for example, dysmenorrhoea, labour pain and pain associated with endometriosis; somatogenic pain; pain associated with nerve and root damage, such as pain associated with peripheral nerve disorders, for example, nerve entrapment and brachial plexus avulsions; pain associated with limb amputation, tic douloureux, neuroma, or vasculitis; diabetic neuropathy, chemotherapy-induced-neuropathy, acute herpetic and postherpetic neuralgia; a typical facial pain, neuropathic lower back pain, and arachnoiditis, trigeminal neuralgia, occipital neuralgia, segmental or intercostal neuralgia, HIV related neuralgias and AIDS related neuralgias and other neuralgias; allodynia, hyperalgesia, burn pain, idiopathic pain, pain caused by chemotherapy; occipital neuralgia, psychogenic pain, brachial plexus avulsion, pain associated with restless legs syndrome; pain associated with gallstones; pain caused by chronic alcoholism or hypothyroidism or uremia or vitamin deficiencies; neuropathic and non-neuropathic pain associated with carcinoma, often referred to as cancer pain, phantom limb pain, functional abdominal pain, headache, including migraine with aura, migraine without aura and other vascular headaches, acute or chronic tension headache, sinus headache and cluster headache; temperomandibular pain and maxillary sinus pain; pain resulting from ankylosing spondylitis; pain caused by increased bladder contractions; post operative pain, scar pain, and chronic non-neuropathic pain such as pain associated with HIV, anthralgia, vasculitis and fibromyalgia in a mammal, comprising administering to a mammal in need of such treatment a therapeutically effective amount of a compound of the formula I or II, or a pharmaceutically acceptable salt thereof.

This invention also relates to a method of treating a disorder or condition selected from mood disorders, such as depression, or more particularly, depressive disorders, for example, major depressive disorder, severe unipolar recurrent major depressive episodes, dysthymic disorder, depressive neurosis and neurotic depression, melancholic depression including anorexia, weight loss, insomnia, early morning waking or psychomotor retardation, atypical depression (or reactive depression) including increased appetite, hypersomnia, psychomotor agitation or irritability; treatment resistant depression; seasonal affective disorder and pediatric depression; premenstrual syndrome, premenstrual dysphoric disorder, hot flashes, bipolar disorders or manic depression, for example, bipolar I disorder, bipolar II disorder and cyclothymic disorder; seasonal affective disorder, conduct disorder and disruptive behavior disorder; stress related somatic disorders and anxiety disorders, such as childhood anxiety disorder, panic disorder with or without agoraphobia, agoraphobia without history of panic disorder, specific phobias (e.g., specific animal phobias), social anxiety disorder, social phobia, obsessive-compulsive disorder, stress disorders including post-traumatic stress disorder and acute stress disorder, and generalized anxiety disorder in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of borderline personality disorder; schizophrenia and other psychotic disorders, for example, schizophreniform disorders, schizoaffective disorders, delusional disorders, brief psychotic disorders, shared psychotic disorders, psychotic disorders due to a general medical condition, psychotic disorders with delusions or hallucinations, substance induced psychotic disorder, psychotic episodes of anxiety, anxiety associated with psychosis, psychotic mood disorders such as severe major depressive disorder; mood disorders associated with psychotic disorders such as acute mania and depression associated with bipolar disorder, mood disrders associated with schizophrenia; and behavioral disturbances associated with mental retardation in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of sleep disorders such as insomnia (e.g., primary insomnia including psychophysiological and idiopathic insomnia, secondary insomnia including insomnia secondary to restless legs syndrome, Parkinson's disease or another chronic disorder, and transient insomnia), somnambulism, sleep deprivation, REM sleep disorders, sleep apnea, hypersomnia, parasomnias, sleep-wake cycle disorders, jet lag, narcolepsy, sleep disorders associated with shift work or irregular work schedules, deficient sleep quality due to a decrease in slow wave sleep caused by medications or other sources, and other sleep disorders in a mammal, comprising administering to a mammal in need of such treatment a therapeutically effective amount of a compound of the formula I or II, or a pharmaceutically acceptable salt thereof.

This invention also relates to a method of increasing slow wave sleep and increasing growth hormone secretion in a human subject comprising administering to a human subject in need of such treatment a therapeutically effective amount of a compound of the formula I or II, or a pharmaceutically acceptable salt thereof.

This invention also relates to a method of treating a disorder or condition selected from the group consisting of respiratory diseases, particularly those associated with excess mucus secretion, such as chronic obstructive airways disease, bronchopneumonia, chronic bronchitis, cystic fibrosis, adult respiratory distress syndrome, and bronchospasm; cough, whooping cough, angiotensin converting enzyme (ACE) induced cough, pulmonary tuberculosis, allergies such as eczema and rhinitis; contact dermatitis, atopic dermatitis, urticaria, and other eczematoid dermatitis; itching, hemodialysis associated itching; inflammatory diseases such as inflammatory bowel disease, psoriasis, osteoarthritis, cartilage damage (e.g., cartilage damage resulting from physical activity or osteoarthritis), rheumatoid arthritis, psoriatic arthritis, asthma, pruritis and sunburn; and hypersensitivity disorders such as poison ivy in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of neurodegenerative disorders, such as Parkinson's disease (PD), Huntington's disease (HD) and Alzheimer's disease (AD); delerium, dementias (e.g., senile dementia of the Alzheimer's type, senile dementia, vascular dementia, HIV-1 associated dementia, AIDS dementia complex (ADC), dementias due to head trauma, Parkinson's disease, Huntington's disease, Pick's disease, Creutzfeldt-Jakob disease, or due to multiple etiologies), amnestic disorders, other cognitive or memory disorders, and behavioral symptoms of dementia in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of Down's syndrome; Sjogren's syndrome, hypertension, hematopoiesis, postoperative neuroma, benign prostatic hypertrophy, periodontal disease, hemorrhoids and anal fissures, infertility, reflex sympathetic dystrophy, hepatitis, tenalgia attendant to hyperlipidemia, vasodilation, fibrosing and collagen diseases such as scleroderma and eosinophilic fascioliasis; and vasospastic diseases such as angina, migraine and Reynaud's disease in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of ophthalmic diseases such as dry eye syndrome, conjunctivitis, vernal conjunctivitis, and the like; and ophthalmic conditions associated with cell proliferation such as proliferative vitreoretinopathy in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of autism, attention deficit hyperactivity disorder (ADHD), angiogenesis (i.e., use for the inhibition of angiogenesis); Reiter's syndrome and anthropathies in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium and withdrawal delerium; and addiction disorders involving addictions to behaviors (e.g., addictions to gambling and other addictive behaviors) in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of Down's syndrome; demyelinating diseases such as multiple sclerosis (MS) and amylolateral sclerosis (ALS) in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of pervasive development disorder, fibromyalgia, human immunodeficiency virus (HIV) infections; HIV encephalopathy; dissociative disorders such as body dysmorphic disorders; eating disorder such as anorexia and bulimia; ulcerative colitis; Crohn's disease; irritable bowel syndrome; chronic pancreatitis, chronic fatigue syndrome; sudden infant death syndrome (SIDS); overactive bladder; lower urinary tract symptoms of overactive bladder; chronic cystitis; chemotherapy induced cystitis; cough, angiotensin converting enzyme (ACE) induced cough, itch, hiccups, premenstrual syndrome, premenstrual dysphoric disorder, amenorrheic disorders such as desmenorrhea; reflex sympathetic dystrophy such as shoulder/hand syndrome; plasma extravasation resulting from cytokine chemotherapy; disorders of bladder function such as chronic cystitis, bladder detrusor hyper-reflexia, inflammation of the urinary tract and urinary incontinence, including urinary urge incontinence, overactive bladder, stress incontinence and mixed incontinence; fibrosing and collagen diseases such as scleroderma and eosinophilic fascioliasis; blood flow disorders caused by vasodilation and vasospastic diseases such as angina and Reynaud's disease; sexual dysfunctions including premature ejaculation and male erectile dysfunction in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of movement disorders such as primary movement disorders, akinesias, dyskinesias (e.g., familial paroxysmal dyskinesia, tardive dyskinesia, tremor, chorea, myoclonus, tics and other dyskinesias) spasticities, Tourette's syndrome, Scott syndrome, palsys (e.g., Bell's palsy, cerebral palsy, birth palsy, brachial palsy, wasting palsy, ischemic palsy, progressive bulbar palsy and other palsys), akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; restless legs syndrome and movement disorders associated with Parkinson's disease or Huntington's disease in a mammal, comprising administering to a mammal in need of such treatment a therapeutically effective amount of a compound of the formula I or II, or a pharmaceutically acceptable salt thereof.

This invention also relates to a method of treating a disorder, or condition selected from the group consisting of mastalgia syndromes, motion sickness, systemic lupus erythematosis and immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, and human-animal interaction stress in dogs) in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of gastrointestinal (GI) disorders, including inflammatory gastrointestinal disorder's such as inflammation bowel disease, disorders caused by *helicobacter pylori* and diseases of the GI tract such as gastritis, proctitis, gastroduodenal ulcers, peptic ulcers, dyspepsia, disorders associated with the neuronal control of viscera, ulcerative colitis, Crohn's disease, irritable bowel syndrome and emesis, including post operative nausea and post operative vomiting, and including acute, delayed or anticipatory emesis (emesis includes emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia) in a mammal, comprising administering to a mammal in need of such treatment a therapeutically effective amount of a compound of the formula I or II, or a pharmaceutically acceptable salt thereof.

This invention also relates to a method of treating a disorder or condition selected from the group consisting of neoplasms, including breast tumours, gastric carcinomas, gastric lymphomas, neuroganglioblastomas and small cell carcinomas such as small cell lung cancer in a mammal, comprising administering to a mammal in need of such treatment a therapeutically effective amount of a compound of the formula I or II, or a pharmaceutically acceptable salt thereof.

The foregoing methods are also referred to herein, collectively, as the "invention methods".

The term "treating", as used herein, refers to reversing, alleviating, inhibiting the progress of, or preventing the disorder or condition to which such term applies, or preventing one or more symptoms of such condition or disorder.

The term "treatment", as used herein, refers to the act of treating, as "treating" is defined immediately above.

DETAILED DESCRIPTION OF THE INVENTION

The compounds of the present invention can be prepared as described in the following reaction schemes and discussion. In the reaction schemes and discussion that follow, $R^1$ through $R^4$ and G, unless otherwise indicated, are defined as above.

α-Substituted-β-aminotetrazoles may be synthesized by the general route outlined in Scheme 1.

SCHEME 1

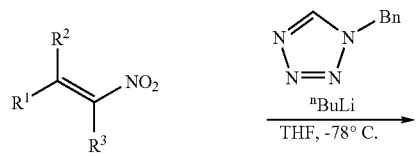

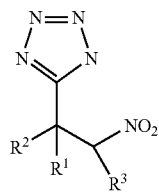

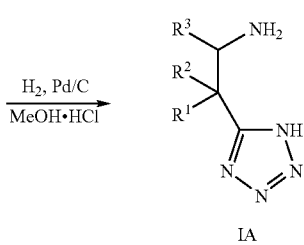

Referring to Scheme 1, a compound of the formula 1 is reacted with 4-benzyltetrazole and n-butyllithium in an appropriate reaction inert solvent, e.g., an ethereal solvent, preferably tetrahydrofuran (THF), at a temperature from about −110° C. to about −78° C., preferably at about −78° C. The desired products of the formula IA can be formed from the corresponding benzyl derivatives of formula 2 using standard methods well known to those of skill in the art, for example, by hydrogenating the compounds of formula 4 with hydrogen gas, using a hydrogen gas pressure of from 1-5 atmospheres, preferably about 3 atmospheres, and a palladium on carbon or platinum dioxide catalyst, in a solvent that is a mixture of hydrochloric or sulfuric acid and either methanol or ethanol, at a temperature from about 0° C. to about room temperature, preferably at about room temperature.

Scheme 2 illustrates a method of synthesizing compounds of the formula IA wherein $R^2$, $R^3$ and $R^4$ are hydrogen and $R^1$ is $R^5$-methyl wherein $R^5$ is hydrogen, $(C_1-C_9)$straight or branched alkyl, $(C_1-C_9)$straight or branched alkoxyalkyl, phenyl-$(C_1-C_3)$straight or branched alkyl, phenylmethoxymethyl, or phenylmethoxy, wherein said phenyl moieties can optionally be substituted with one or two substituents selected, independently, from halo and $(C_1-C_3)$ alkyl.

SCHEME 2

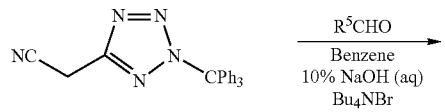

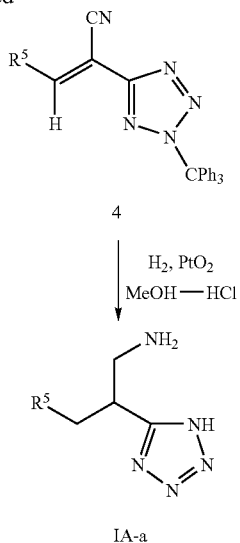

Referring to Scheme 2, the acetonitrile derivative of formula 3 wherein Ph is phenyl, is converted into a compound of the formula 4 by reacting it with an aldehyde of the formula $R^5$CHO, tetrabutylammonium bromide and aqueous sodium hydroxide or potassium hydroxide, preferably 10% sodium hydroxide, in benzene, at a temperature from about 40° C. to about the reflux temperature of the reaction mixture, preferably at about the reflux temperature. The desired compounds of formula IA-a can be formed from the corresponding compounds of formula 4 using standard methods well known to those of skill in the art, for example, by hydrogenating the compounds of formula 4, using a hydrogen gas pressure of from 1-5 atmospheres, preferably about 3 atmospheres, and a platinum dioxide catalyst or other suitable hydrogenation catalyst (e.g., palladium on carbon or Raney nickel) in a solvent that is a mixture of methanol or ethanol and hydrochloric or sulfuric acid, at a temperature from about 0° C. to about room temperature, preferably at about room temperature.

The tetrazole derivative of formula 3, which is the starting material in Scheme 2, can be prepared as illustrated below in Scheme 3.

SCHEME 3

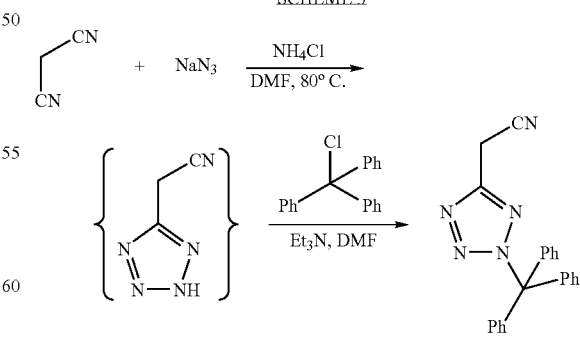

Referring to Scheme 3, malononitrile is reacted with sodium azide in dimethylformamide (DMF), in the presence of ammonium chloride, at a temperature of about 80° C., to produce 5-cyanomethyltetrazole, which is then reacted, in situ or following isolation, with triphenylchloromethane in DMF, in the presence of triethylamine, at a temperature of about 25° C.

Scheme 4 illustrates the synthesis of compounds of the formula IA wherein $R^2$, $R^3$ and $R^4$ are hydrogen and $R^1$ is $CHR^6R^7$ from ketones of the formula $R^6(C=O)R^7$. These compounds are referred to as compounds of the formula IA-a.

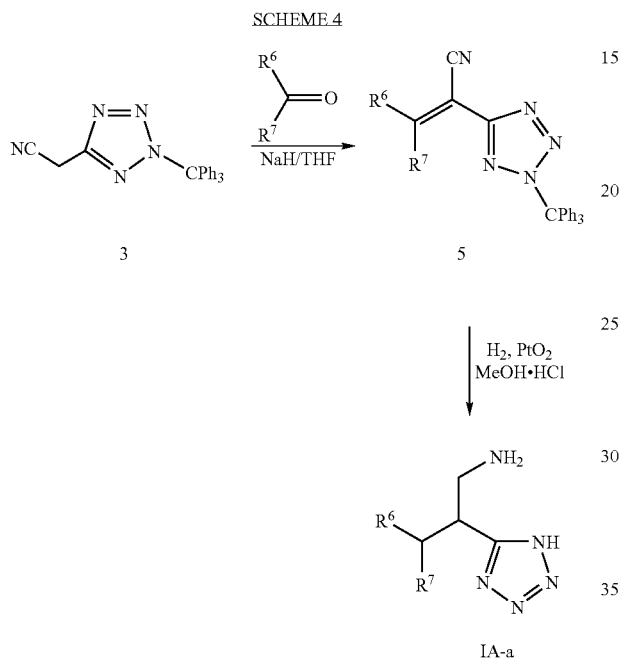

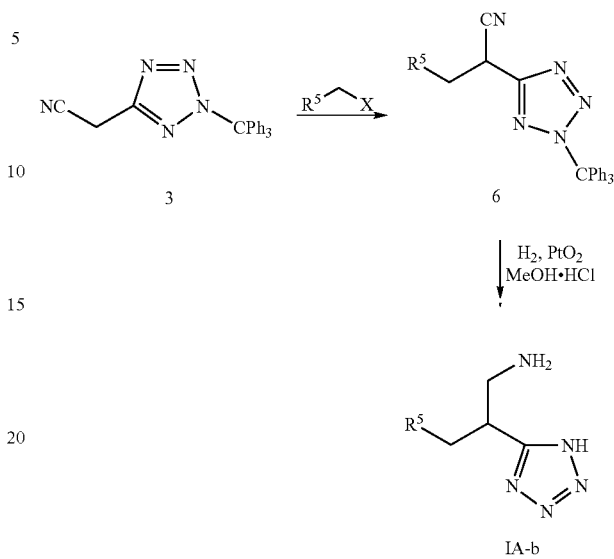

Referring to Scheme 4, compounds of the formula 5 can be prepared from the corresponding ketones of the formula $R^1(C=O)R^2$ by reacting such ketones with the compound of formula 3 in an ethereal solvent, toluene or benzene, preferably in THF, in the presence of sodium hydride or potassium hydride, preferably sodium hydride, at a temperature from about 0° C. to about room temperature. Preferably, the reaction is begun at about 0° C. and allowed to warm gradually to room temperature. The desired compounds of formula IA-a can then be formed from the corresponding compounds of formula 5 using standard methods well known to those of skill in the art, for—example—, by hydrogenating the compounds of formula 5 with hydrogen gas, using a hydrogen gas pressure of from 1-5 atmospheres, preferably about 3 atmospheres, and a platinum dioxide catalyst or other suitable hydrogenation catalyst (e.g., palladium on carbon or Raney nickel) in a mixture of methanol and hydrochloric or sulfuric acid, at a temperature from about 0° C. to about room temperature, preferably at about room temperature.

Scheme 5 illustrates a method of synthesizing compounds of the formula IA wherein $R^2$ is hydrogen and $R^1$ is $CH_2R^5$ by alkylating the acetonitrile derivative of formula 3 with an alkyl halide of the formula $R^5CH_2X$, wherein $R^5$ is defined as above and X is chloro or bromo, and then hydrogenating the resulting product. The resulting compounds are referred to as compounds of the formula IA-b.

Referring to Scheme 5, the acetonitrile derivative of formula 3 is reacted with an alkyl halide of the formula $R^5CH_2X$, wherein $R^5$ and X are defined as above, in an appropriate reaction inert solvent such as benzene, toluene or an ethereal solvent, preferably THF, in the presence of sodium hydride or potassium hydride, preferably sodium hydride, at a temperature from about −20° C. to about 25° C., preferably at about 0° C., to form the corresponding compounds of formula 6. Hydrogenation of the compounds of formula 6, using standard procedures well known to those of skill in the art and described above for forming compounds of the formula IA-a according to the procedure of Scheme 4, yields the corresponding compounds of the formula IA-b.

The preparation of compounds of the formula IA by dialkylating the acetonitrile derivative of formula 3 and then hydrogenating the resulting product is illustrated in Scheme 6 below.

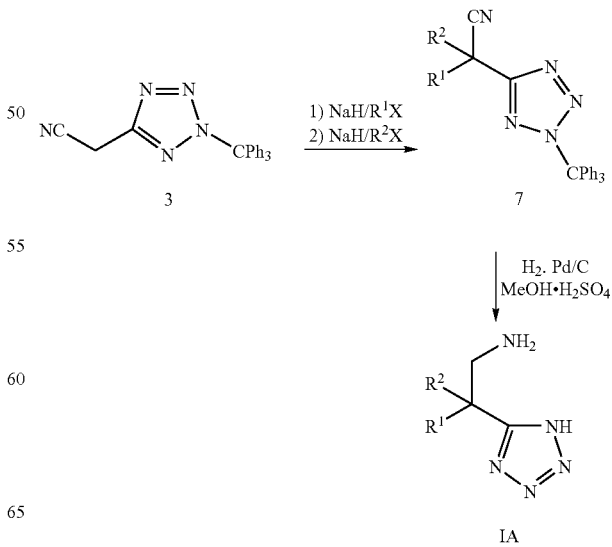

Referring to Scheme 6, the acetonitrile derivative of formula 3 is reacted first with a compound of the formula $R^1X$, wherein X is defined as above, and then with a compound of the formula $R^2X$, wherein X is defined as above, to yield the corresponding compound of formula 7. These reactions are typically conducted in toluene, benzene or an ethereal solvent, in the presence of sodium hydride or potassium hydride, at a temperature from about −20° C. to about 25° C. They are preferably conducted in THF, in the presence of sodium hydride, beginning the reaction at about 0° C. and allowing the reaction mixture to gradually warm to room temperature. The desired compounds of formula IA can then be formed from the corresponding compounds of formula 7 using standard methods well known to those of skill in the art, for example, by hydrogenating the compounds of formula 7 with hydrogen gas, using a hydrogen gas pressure of from 1-5 atmospheres, preferably about 3 atmospheres, and a platinum dioxide catalyst or other suitable hydrogenation catalyst (e.g., palladium on carbon or Raney nickel) in a mixture of methanol and hydrochloric or sulfuric acid, at a temperature from about 0° C. to about room temperature, preferably at about room temperature.

Scheme 7 illustrates the preparation of compounds of the formula II wherein $R^3$ and $R^4$ are hydrogen, G is 5-tetrazolyl and $R^2$ is hydrogen. These compounds are referred to as compounds of the formula IIA.

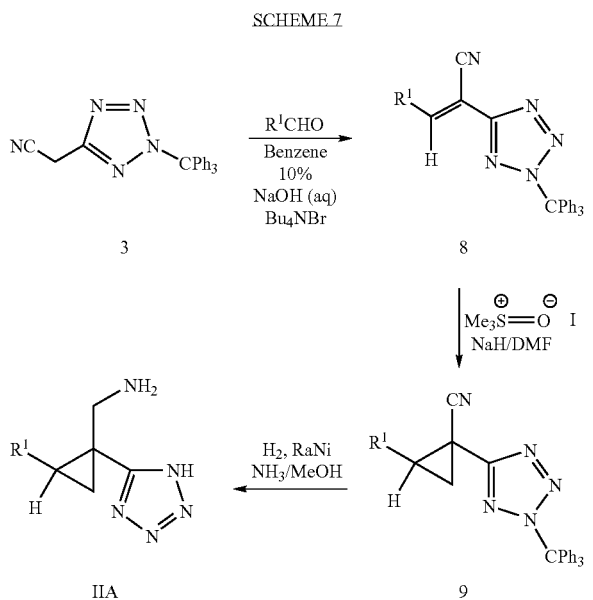

Referring to Scheme 7, the acetonitrile derivative of formula 3 is reacted with an aldehyde of the formula $R^1CHO$, tetrabutylammonium bromide and aqueous sodium hydroxide or potassium hydroxide, preferably 10% sodium hydroxide, in benzene at a temperature from about 40° C. to about the reflux temperature of the reaction mixture, preferably at about the reflux temperature, to form the corresponding compound of formula 8. Cyclization of the unsaturated tetrazole derivative of formula 8 to form the cyclopropyl intermediate of formula 9 can be accomplished by reacting the compound of formula 8 with trimethylsulfoxonium iodide and sodium hydride in dimethylformamide (DMF), at a temperature from about 0° C. to about 25° C., preferably at about room temperature. Preferably, a dispersion of sodium hydride in mineral oil is added to trimethylsulfoxonium iodide in DMF, and, after stirring, the compound of formula 3 is added dropwise.

The desired compounds of formula IIA can be formed from the corresponding compounds of formula 9 using standard methods well known to those of skill in the art, for example, by hydrogenating the compounds of formula 9, using a hydrogen gas pressure of from 1-5 atmospheres, preferably about 3 atmospheres, and a platinum dioxide catalyst or other suitable hydrogenation catalyst (e.g., palladium on carbon or Raney nickel) in a mixture of methanol and hydrochloric or sulfuric acid, at a temperature from about 0° C. to about room temperature, preferably at about room temperature.

The synthesis of compounds of the formula II wherein G is 4-tetrazolyl, and $R^3$ and $R^4$ are hydrogen is depicted in Scheme 8. These compounds are referred to as compounds of the formula IIB.

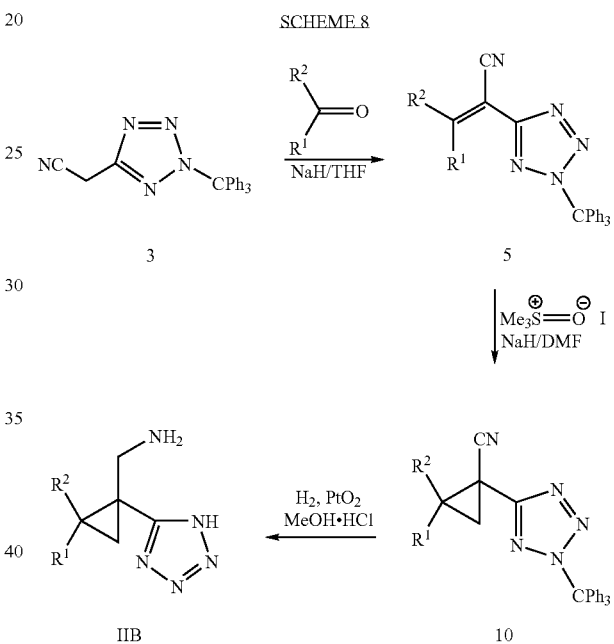

Referring to Scheme 8, compounds of the formula 5 can be prepared from the corresponding ketones of the formula $R^1(C=O)R^2$ by reacting such ketones with the compound of formula 3 in an ethereal solvent, toluene or benzene, preferably in THF, in the presence of sodium hydride or potassium-hydride, preferably sodium hydride, at a temperature from about 0° C. to about room temperature. Preferably, the reaction is begun at about 0° C. and allowed to warm gradually to room temperature. The resulting compounds of formula 5 can be converted into the corresponding compounds of formula IIB using the procedures analogous to those described above for converting compounds of the formula 8 into the corresponding compounds of formula IIA.

Scheme 10 depicts the preparation of compounds of the formula II wherein G is 5-oxodiazolone and $R^1$ and $R^2$, together with the carbon to which they are attached, form a cyclopentyl, cyclohexyl or cycloheptyl ring. These compounds are referred to as compounds of the formula IIC. Scheme 9 depicts the synthesis of cyclopropyl derivatives that are starting materials and intermediates used in the procedure of Scheme 10.

SCHEME 9

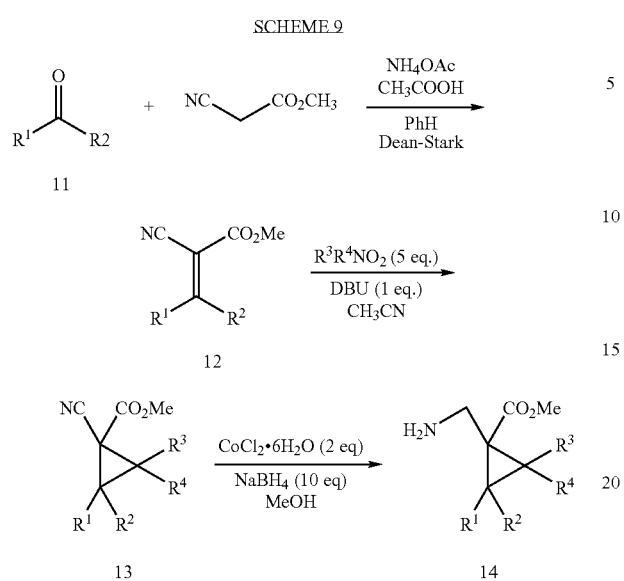

Referring to Scheme 9, compounds of formula 11 can be converted into the corresponding compounds of the formula 12 by reacting them with a compound of the formula NCCH$_2$CO$_2$CH$_3$, ammonium acetate and glacial acetic acid in benzene, at a temperature from about 40° C. to about the reflux temperature, preferably at about the reflux temperature. This reaction is typically conducted with azeotropic removal of water, e.g., using a Dean-Stark trap, molecular sieves, magnesium sulfate, etc. Reaction the compounds of formula 12 with the appropriate compound of formula R$^4$R$^3$NO$_2$, in the presence of 1,8-diazabicyclo[5.4.0]undec-7-one (DBU), in an acetonitrile solvent, or in the presence of potassium carbonate in an ethanol solvent, yields the corresponding compounds of formula 13. Preferably, one equivalent of DBU is used per five equivalents of R$^4$R$^3$NO$_2$. This reaction is generally carried out at a temperature from about 60° C. to about 80° C., preferably at about 60° C.

The cyano substituted esters of formula 13 can be converted into the corresponding aminomethyl substituted esters of formula 14 by reacting them with cobalt chloride hexahydrate and sodium or ammonium borohydride in ethanol or a mixture of a lower alcohol and water, at a temperature from about 0° C. to about 40° C. Preferably, two equivalents of cobalt chloride hexahydrate and 10 equivalents of sodium borohydride are used, and the reaction is conducted in methanol at about room temperature.

Scheme 10 illustrates the synthesis of compounds of the formula II wherein G is 5-oxadiazolone. These compounds are referred to as compounds of the formula IIC.

SCHEME 10

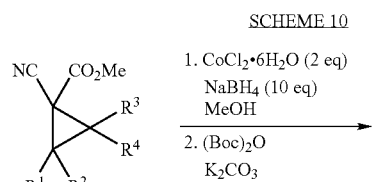

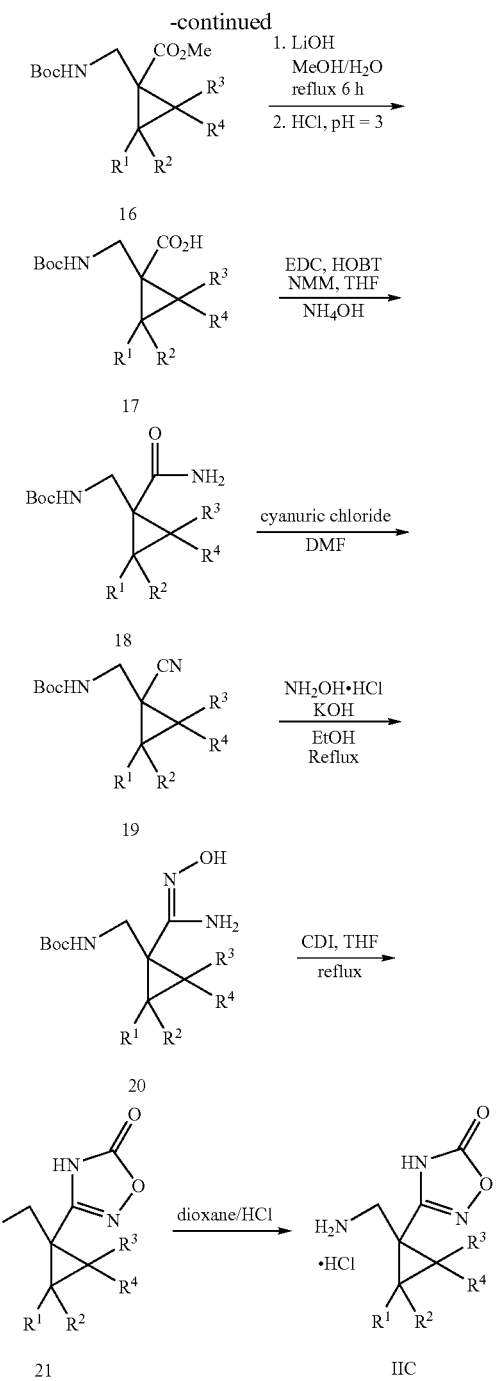

Referring to Scheme 10, compounds of the formula 13 can be converted into the corresponding compounds of the formula 16 by reacting them with cobalt chloride hexahydrate and sodium borohydride in ethanol or a mixture of a lower alcohol and water, at a temperature from about 0° C. to about 40° C., and then protecting the amino nitrogen. Preferably, two equivalents of cobalt chloride hexahydrate and 10 equivalents of sodium borohydride are used, and the reaction is conducted in methanol at about room temperature. The amino group of the resulting compound is then protected by reacting such compound with di-tert-butyidi-carbonate in dichloromethane. The latter reaction is also generally conducted at a temperature from about 0° C. to about 40° C., and is preferably conducted at about room temperature.

The corresponding compounds of formula 17 can be prepared as follows. The resulting compounds of formula 16 are reacted with lithium hydroxide in methanol or another lower alcohol, e.g., ethanol or n-butanol, at a temperature from about 50° C. to about 70° C., preferably at the reflux temperature, to form the corresponding lithium carboxylates, and then the resulting carboxylates are reacted with a strong mineral acid. Preferably, the carboxylates are converted into the corresponding acids in situ by cooling the reaction mixture to a temperature between about 0° C. and about 25° C. and adding enough hydrochloric acid to bring the pH of the mixture to about 3.0.

The carboxylic acids of formula 17 can be converted into the corresponding amides of formula 18 by reacting them with NMM (N-methylmorpholine), hydroxybenxotriazole and EDC (1-(3-dimethylaminopropyl)-3-ethylcarbodiimide) in tetrahydrofuran (THF), stirring the reaction for about 3 hours and then adding concentrated aqueous ammonium hydroxide. These reactions are generally conducted at a temperature from about 0° C. to about room temperature, and are preferably conducted at about room temperature. Reaction of the amides of formula 18 with cyanuric chloride in DMF, at a temperature from about −20° C. to about room temperature, preferably at about 0° C., yields the corresponding cyano derivatives of formula 19.

Reaction of the cyano derivatives of formula 19 with hydroxylamine hydrochloride and ground potassium or sodium hydroxide, in a methanol or ethanol solvent, at about the reflux temperature, yields the corresponding compounds of formula 20. The compounds of formula 20 can be cyclized to form the corresponding nitrogen protected oxadiazolones of formula 21 by reacting them with carbonyldiimidazole in an ethereal solvent such as THF, glyme, or dioxane preferably THF, at a temperature from about 40° C. to about the reflux temperature of the reaction mixture, preferably at about the reflux temperature.

Removal of the nitrogen protecting group from the compounds of formula 21 yields the hydrochloride salts (or other salts) of the desired compounds of formula IIC. This is generally accomplished by reacting the compounds of formula 21 with hydrochloric acid, or another appropriate acid to produce the desired salts (e.g., trifluoroacetic acid to produce the acetate salts) at a temperature from about 0° C. to about 40° C., preferably at about 25° C.

All that is required to practice the method of this invention is to administer a compound of the formula I, or a pharmaceutically acceptable salt thereof, in an amount that is therapeutically effective to treat one or more of the disorders or conditions referred to above. Such therapeutically effective amount will generally be from about 1 to about 300 mg/kg of subject body weight per day. Typical doses will be from about 10 to about 5000 mg/day for an adult subject of normal weight. In a clinical setting, regulatory agencies such as, for example, the Food and Drug Administration ("FDA") in the U.S. may require a particular therapeutically effective amount.

In determining what constitutes an effective amount or a therapeutically effective amount of a compound of the formula I, or a pharmaceutically acceptable salt thereof, for treating one or more of the disorders or conditions referred to above according to the invention method, a number of factors will generally be considered by the medical practitioner or veterinarian in view of the experience of the medical practitioner or veterinarian, published clinical studies, the subject's age, sex, weight and general condition, as well as the type and extent of the disorder or condition being treated, and the use of other medications, if any, by the subject. As such, the administered dose may fall within the ranges or concentrations recited above, or may vary outside, ie., either below or above, those ranges depending upon the requirements of the individual subject, the severity of the condition being treated, and the particular therapeutic formulation being employed. Determination of a proper dose for a particular situation is within the skill of the medical or veterinary arts. Generally, treatment may be initiated using smaller dosages of the alpha2delta ligand that are less than optimum for a particular subject. Thereafter, the dosage can be increased by small increments until the optimum effect under the circumstance is reached. For convenience, the total daily dosage may be divided and administered in portions during the day, if desired.

Pharmaceutical compositions of a compound of the formula I, or a pharmaceutically acceptable salt thereof, are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses.

Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations.

The compositions to be employed in the invention can also contain other components such as coloring agents, flavoring agents, and/or preservatives. These materials, if present, are usually used in relatively small amounts. The compositions can, if desired, also contain other therapeutic agents commonly employed to treat the disorder or condition being treated.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present, for example, up to about 95%.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The degree of binding to the α2δ subunit can be determined using the radioligand binding assay using [$^3$H]gabapentin and the α2δ subunit derived from porcine brain tissue, as described by N. S. Gee et al., *J. Biol. Chem.*, 1996, 271:5879-5776.

The radioligand binding assay using [$^3$H]-gabapentin and the α2δ-subunit derived from porcine brain tissue was used (See, Gee, Nicolas S et al. "*The novel anticonvulsant drug, gabapentin (Neurontin), binds to the α2δ subunit of a calcium channel*" *J. Biol. Chem.* (1996), 271(10), 5768-76). Compounds of the invention bind with nanomolar to micromolar affinity for the α2δ protein. For example, the title compound of Example 26 exhibited an IC$_{50}$ value of 712 nM, the title compound of Example 11 exhibited an IC$_{50}$ value of 93 nM, and the title compound of Example 19 exhibited an IC50 of 82 nM.

The In vivo activity of compounds of this invention can be determined in animal models of hyperalgesia (See Sluka, K., et al. 2001, "Unilateral Intramuscular Injections Of Acidic Saline Produce A Bilateral, Long-Lasting Hyperalgesia", *Muscle Nerve* 24: 37-46; Dixon, W., 1980, "Efficient analysis of experimental observations". *Ann Rev Pharmacol Toxicol* 20:441-462; Randall L. O. and Selifto J. J., "A Method For Measurement Of Analgesic Activity On Inflamed Tissue," *Arch. Int. Pharmacodyn.*, 1957;4:409-419; Hargreaves K., Dubner R., Brown F., Flores C., and Joris J. "A New And Sensitive Method For Measuring Thermal Nociception In Cutaneous Hyperalgesia". Pain. 32:77-88, 1988.), anxiety (Vogel. J R, Beer B, and Clody DE, "A Simple And Reliable Conflict Procedure For Testing Anti-Anxiety Agents", *Psychopharmacologia* 21:1-7, 1971).

The following Examples illustrate the preparation of the compounds of the present invention. Melting points are uncorrected. NMR data are reported in parts per million and are referenced to the deuterium lock signal from the sample solvent.

EXAMPLES

Example 1

4-Methyl-2-(1H-tetrazol-5-yl)-pentylamine

A. 1-Benzyl-5-(3-methyl-1-nitromethyl-butyl)-1H-tetrazole

To a solution of 1-benzyl-1H-tetrazole[1] (0.25 g, 1.56 mmol) in 7.0 mL THF at −78° C. was added n-butyllithium (1.6M solution in hexanes, 1.17 mL, 1.87 mmol) slowly dropwise over 5 min until the yellow color persisted (ca. 1.0 equiv). The mixture was stirred at −78° C. for 15 min at which time 4-methyl-1-nitropent-1-ene (0.20 g, 1.56 mmol) in 1 mL THF was added dropwise. The mixture was stirred at −78° C. for 20 min, then warmed directly to ambient temperature and quenched with sat. NH$_4$Cl (aq). The mixture was extracted with EtOAc, and the organic phase dried (Na$_2$SO$_4$) and concentrated. Flash chromatography of the residue (15→20→25% EtOAc/hexanes) provided 0.27 g (60%) of 1-benzyl-5-(3-methyl-1-nitromethyl-butyl)-1H-tetrazole as a colorless oil: $^1$H NMR (CDCl$_3$) δ 7.37 (m, 3H), 7.22 (m, 2H), 5.72 (d, J=15.6 Hz, 1H, —PhCHHN—), 5.50 (d, J=15.6 Hz, 1H, —PhCHHN—), 4.69 (dd, J=14.6, 9.8 Hz, 1H, —CHCHHNO$_2$), 4.56 (dd, J=14.6, 5.1 Hz, 1H, —CHCHHNO$_2$), 3.72 (m, 1H, —CHCH$_2$NO$_2$), 1.47 (m, 2H, —CHCH$_2$CH—), 1.19 (hept, J=6.6 Hz, 1H, CH$_3$CH—), 0.65 (d, J=6.6 Hz, 3H, CH$_3$—), 0.62 (d, J=6.6 Hz, 3H, CH$_3$—). [1]Preparation: Satoh, Y.; Marcopulos, N. "Application of 5-Lithiotetrazoles in Organic Synthesis" *Tetrahedron Lett.* 1995, 36(11), 1759-1762.

B. 4-Methyl-2-(1H-tetrazol-5-yl)-pentylamine

To a solution of 1-benzyl-5-(3-methyl-1-nitromethyl-butyl)-1H-tetrazole (1.41 g, 4.87 mmol) in MeOH (50 mL) was added 20% Pd/C (0.20 g) and concentrated HCl (0.6 g). The mixture was hydrogenated in a Parr shaker at 48 psi for 70 h, filtered, and concentrated. The residue was dissolved in 5 mL H$_2$O and loaded onto a plug of DOWEX-50WX4-100 ion exchange resin. The column was eluted first with 100 mL H$_2$O, then 50 mL 5% NH$_4$OH (aq), and finally with 50 mL 10% NH$_4$OH aq). The alkaline fractions were concentrated, and the solid obtained was dissolved in the minimum amount of MeOH. The solid was precipitated from MeOH with EtOAc, the solvent was withdrawn with a pipet, and the solid was then triturated with hot EtOAc. The solvent was drawn off with a pipet upon cooling and the remaining solid dried under vacuum to provide 0.33 g (40%) of 4-methyl-2-(1H-tetrazol-5-yl)-pentylamine as a colorless solid, mp>240° C. (dec). $^1$H NMR (D$_2$O) δ 3.31 (m, 1H, —CHCH$_2$NH$_2$), 3.10 (m, 2H, —CH$_2$NH$_2$), 1.53 (m, 1H, —CHCHHCH—), 1.35 (m, 1H, —CHCHHCH—), 1.03 (m, 1H, CH$_3$CH—), 0.66 (d, J=6.6 Hz, 3H, CH$_3$—), 0.61 (d, J=6.6 Hz, 3H, CH$_3$—). LRMS: m/z 168.0 (M−1). Anal. Calcd for C$_7$H$_{15}$N$_5$: C, 49.68; H, 8.93; N, 41.38. Found: C, 49.51; H, 8.90; N, 41.20.

Example 2

3-Methyl-2-(1H-tetrazol-5-yl)-butylamine

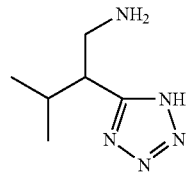

$^1$H NMR (D$_2$O) δ 3.25 (m, 2H, —C$\underline{H}_2$NH$_2$), 3.02 (m, 1H, —C$\underline{H}$CH$_2$—), 1.85 (m, 1H, CH$_3$C$\underline{H}$—), 0.74 (d, J=6.6 Hz, 3H, C$\underline{H}_3$—), 0.54 (d, J=6.6 Hz, 3H, C$\underline{H}_3$—). Anal. Calcd for C$_6$H$_{13}$N$_5$: C, 46.43; H, 8.44; N, 45.12. Found: C, 46.20; H, 8.34; N, 44.51.

Example 3

4,4-Dimethyl-2-(1H-tetrazol-5-yl)-pentylamine

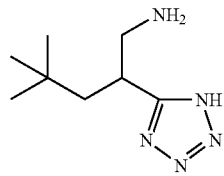

$^1$H NMR (D$_2$O) δ 2.94 (m, 1H, —CH$_2$C$\underline{H}$CH$_2$—), 2.66 (m, 2H, —C$\underline{H}_2$NH$_2$), 1.32 (m, 1H, —C$\underline{H}$HCH—), 1.07 (m, 1H, —CH$\underline{H}$CH—), 0.16 (s, 9H). Anal. Calcd for C$_8$H$_{17}$N$_5$: C, 52.43; H, 9.35; N, 38.22. Found: C, 52.37; H, 9.52; N, 35.37.

Example 4

2-(1H-tetrazol-5-yl)-pentylamine

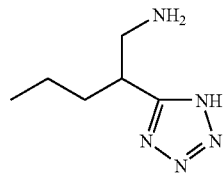

$^1$H NMR (D$_2$O) δ 3.13 (m, 3H, —C$\underline{H}$C$\underline{H}_2$NH$_2$), 1.51 (m, 2H, —C$\underline{H}_2$CH—), 0.91 (m, 2H, CH$_3$C$\underline{H}_2$—), 0.61 (t, J=7.3 Hz, 3H, C$\underline{H}_3$—). LRMS: m/z 153.9 (M−1). Anal. Calcd for C$_6$H$_{13}$N$_5$: C, 46.43; H, 8.44; N, 45.12. Found: C, 46.96; H, 8.50; N, 43.77.

Example 5

4R,8-Dimrthyl-2-(1H-tetrazol-5-yl)-nonylamine

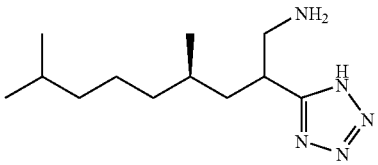

Prepared as a 1:1 mixture of diastereomers at position 2. Anal. Calcd for C$_{12}$H$_{25}$N$_5$: C, 60.21; H, 10.53; N, 29.26. Found: C, 59.87; H, 10.25; N, 28.72.

Example 6

2-Phenyl-2-(1H-tetrazol-5-yl)-ethylamine

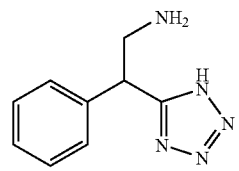

$^1$H NMR (CD$_3$OD) δ 7.28 (m, 5H), 4.60 (m, 1H, —C$\underline{H}$Ph), 3.68 (dd, J=12.9, 9.0 Hz, 1H, —C$\underline{H}$HNH$_2$), 3.49 (dd, J=12.7, 6.6 Hz, 1H, —CH$\underline{H}$NH$_2$). Anal. Calcd for C$_9$H$_{11}$N$_5$: C, 57.13; H, 5.86; N, 37.01. Found: C, 56.43; H, 5.95; N, 36.12.

Example 7

4-Propyl-2-(1H-tetrazol-5-yl)-heptylamine

A. (2-Trityl-2H-tetrazol-5-yl)-acetonitrile

Malononitrile (37.6 g, 0.57 mol), sodium azide (37.0 g, 0.57 mol), ammonium chloride (30.2 g, 0.57 mol), and DMF (400 mL) were charged to a reaction vessel. The vessel was placed under a nitrogen gas purge, equipped with a thermocouple, and stirred with a mechanical stirrer at room temperature for 30 minutes. The thick slurry was heated to 80° C. and stirred at that temperature for 2 h. $^1$H NMR analysis of a sample showed the reaction to be complete. The mixture was cooled to ambient temperature, at which time triethylamine (159 mL, 1.14 mol) and trityl chloride (159 g, 0.57 mol) were added. The mixture was stirred for 16 hours at ambient temperature. TLC analysis showed that the reaction had gone to completion. The reaction mixture was filtered through a fritted funnel and the solids (NH$_4$Cl salts) were washed with ethyl acetate (1.5L×2). The organic layer was washed with H$_2$O (1L×3) and the aqueous portions were combined and extracted with another part of ethyl acetate (1L). The two organic portions were combined and washed with water (1L), brine, and dried with MgSO$_4$. The sample was concentrated in vacuo to a brown solid. A crude 145 grams of material was added to 400 mL of ethyl acetate and heated to reflux. n-Hexanes (400 mL) was added to the hot solution dropwise over 15 min with continued refluxing. The solution became cloudy and was then cooled slowly to The title compounds of Examples 2 through 6 were prepared using a procedure analogous to that of Example 1.

ambient temperature as a granular solid precipitated from the solution. The granular solid was collected with a fritted funnel and dried in a vacuum oven for 16 h. Low yields for this reaction prompted us to reexamine the NH₄Cl salts that were filtered away during the first step of purification. The salts were slurried with ethyl acetate (600 mL) for several minutes. The solids were filtered once again, washed with ethyl acetate, and the organic mother liquor was concentrated in vacuo to a white solid. The two batches of clean product were combined to give 135 grams (0.38 mol, 69% yield) of (2-trityl-2H-tetrazol-5-yl)-acetonitrile. ¹H NMR (CDCl₃): 4.06 (s, 2H), 7.09 (m, 6H), 7.36 (m, 9H). Anal. Caldc. for C₂₂H₁₇N₅: C, 75.19; H, 4.83; N, 19.93. Found: C, 75.11; H, 4.98; N, 20.06.

B. 4-Propyl-2-(2-trityl-2H-tetrazol-5-yl)-hept-2-enenitrile

To a solution of (2-trityl-2H-tetrazol-5-yl)-acetonitrile (2.0 g, 5.69 mmol) in 25 mL benzene was added 2-n-propylvaleraldehyde (0.87 g, 6.79 mmol), 25 mL 10% NaOH (aq), and tetrabutylammonium bromide (50 mg). The mixture was stirred for 1 h, then poured into EtOAc. The phases were separated, and the organic phase dried (MgSO₄) and concentrated. Flash chromatography of the residue (10→15% EtOAc/hexanes) provided 1.66 g (64%) of 4-propyl-2-(2-trityl-2H-tetrazol-5-yl)-hept-2-enenitrile as a colorless solid. ¹H NMR (CDCl₃) δ 7.34 (m, 10H, —CHCH=C—), 7.09 (m, 6H), 2.86 (m, 1H, —CH₂CH—), 1.30-1.59 (m, 8H, —CH₂CH₂—), 0.90 (t, J=7.1 Hz, 6H, CH₃—).

C. 4-Propyl-2-(1H-tetrazol-5-yl)-heptylamine

To a solution of 4-propyl-2-(2-trityl-2H-tetrazol-5-yl)-hept-2-enenitrile (1.60 g, 3.47 mmol) in 50 mL 1:1 MeOH:THF was added PtO₂ (0.1 g), concentrated HCl (1.09 g), and the mixture was hydrogenated in a Parr shaker at 48 psi for 30 h. The mixture was filtered and concentrated. Flash chromatography of the residue on silica gel (0.25:1.25:3.5 conc. NH₄OH (aq):MeOH:CH₂Cl₂), followed by a second column using the same conditions, provided 0.40 g (51%) of 4-propyl-2-(1H-tetrazol-5-yl)-heptylamine as a colorless solid. ¹H NMR (D₂O) δ 3.29 (m, 1H, —CHCH₂NH₂), 3.09 (m, 2H, —CH₂NH₂), 1.56 (m, 1H, —CHCHHCH—), 1.37 (m, 1H, —CHCHHCH—), 0.80-1.07 (m, 9H, —CH₂CHCH₂—, —CH₂CH₂—), 0.58 (t, J=6.6 Hz, 3H, CH₃—), 0.47 (t, J=6.6 Hz, 3H, CH₃—). Anal. Calcd for C₁₁H₂₃N₅: C, 58.63; H, 10.29; N, 31.08. Found: C, 57.87; H, 10.04; N, 30.73.

The title compounds of Examples 8 through 17 were prepared according to a procedure analogous to that described in Example 7.

Example 8

4-Ethyl-2-(1H-tetrazol-5-yl)-hexylamine

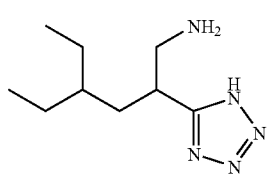

¹H NMR (D₂O) δ 3.33 (m, 1H, —CHCH₂NH₂), 3.16 (m, 2H, —CH₂NH₂), 1.57 (m, 1H, —CHCHHCH—), 1.45 (m, 1H, —CHCHHCH—), 0.91-1.20 (m, 4H, CH₃CH₂—), 0.70 (m, 1H, —CH₂CHCH₂—), 0.61 (t, J=7.3 Hz, 3H, CH₃—), 0.53 (t, J=7.6 Hz, 3H, CH₃—). ¹³C NMR (CD₃OD) □ 161.70, 43.79, 37.43, 36.27, 33.13, 25.23, 24.33, 9.73, 9.32. LRMS: m/z 196.2 (M−1). Anal. Calcd for C₉H₁₉N₅: C, 54.79; H, 9.71; N, 35.50. Found: C, 51.98; H, 9.27; N, 35.96.

Example 9

4-Methyl-2-(1H-tetrazol-5-yl)-hexylamine

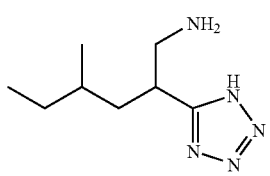

Unknown mixture of diastereomers. LRMS: m/z 182.1 (M−1). Anal. Calcd for C₈H₁₇N₅: C, 52.43; H, 9.35; N, 38.22. Found: C, 51.95; H, 9.20; N, 37.96.

Example 10

4-Ethyl-2-(1H-tetrazol-5-yl)-octylamine

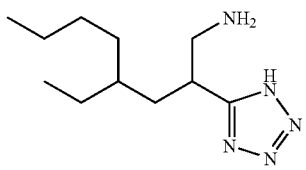

Unknown mixture of diastereomers. Anal. Calcd for C₁₁H₂₃N₅: C, 58.63; H, 10.29; N, 31.08. Found: C, 57.88; H, 9.78; N, 30.81.

Example 11

4,4-Dimethyl-2-(1H-tetrazol-5-yl)-heptylamine

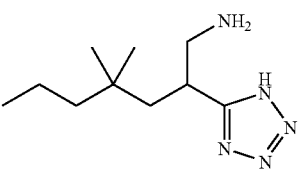

¹H NMR (CD₃OD) δ 3.42 (m, 1H, —CHCH₂NH₂), 3.10 (m, 2H, —CHNH₂), 1.95 (dd, J=13.9, 9.8 Hz, 1H, —CHHCMe₂), 1.52 (dd, J=13.9, 2.7 Hz, 1H, —CHHCMe₂), 1.03-1.19 (m, 4H, —CH₂CH₂CH₃), 0.77 (t, J=6.8 Hz, 3H, CH₃CH₂—), 0.74 (s, 3H), 0.72 (s, 3H).

Example 12

5,5-Dimethyl-2-(1H-tetrazol-5-yl)-hexylamine

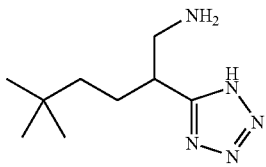

$^1$H NMR (D$_2$O) δ 3.15 (m, 3H, —C<u>H</u>C<u>H</u>$_2$NH$_2$), 1.56 (m, 2H, —C<u>H</u>$_2$CHCH$_2$—), 0.93 (m, 1H, —CC<u>H</u>HCH$_2$—), 0.63 (m, 1H, —CCH<u>H</u>CH$_2$—), 0.59 (s, 9H, C<u>H</u>$_3$—). LRMS: m/z 196.2 (M−1).

Example 13

2-(1H-tetrazol-5-yl)-octylamine

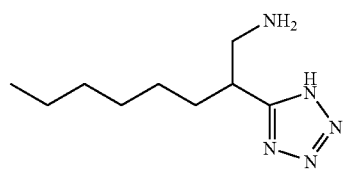

$^1$H NMR (D$_2$O) δ 3.14 (m, 3H, —C<u>H</u>C<u>H</u>$_2$NH2), 1.57 (m, 2H, —C<u>H</u>$_2$CHCH$_2$—), 0.89-0.98 (m, 8H, CH$_3$[C<u>H</u>$_2$]$_4$—), 0.60 (m, 3H, C<u>H</u>$_3$—). LRMS: m/z 196.2 (M−1).

Example 14

5R,9-Dimethyl-2-(1H-tetrazol-5-yl)-decylamine

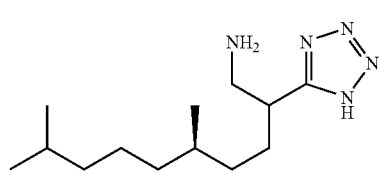

Prepared as a 1:1 mixture of diastereomers at position 2. mp 185° C. (dec). $^1$H NMR (CD$_3$OD) δ 3.36 (m, 1H, —CH<u>H</u>NH$_2$), 3.24 (m, 2H, —C<u>H</u>HNH$_2$, —C<u>H</u>CH$_2$NH$_2$), 1.76 (m, 2H, —C<u>H</u>[CH$_3$]$_2$, —CH<u>H</u>CHCH$_2$NH$_2$), 1.48 (m, 1H, —C<u>H</u>HCHCH$_2$NH$_2$), 1.36 (m, 1H, —CH<u>H</u>CHCH$_3$), 1.22 (m, 4H, —C<u>H</u>HCHCH$_3$, —C<u>H</u>$_2$CHCH$_3$, —C<u>H</u>CH$_3$), 1.10 (m, 4H—C<u>H</u>$_2$CH$_2$—), 0.84 (m, 9H, —C<u>H</u>$_3$). LRMS: m/z 254.2 (M+1). HRMS: [M+H]+Calcd for C$_{13}$H$_{27}$N$_5$: 254.2344. Found: 254.2339.

Example 15

3-Cyclohexyl-2-(1H-tetrazol-5-yl)-propylamine

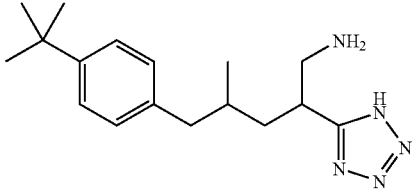

mp>250° C. (dec.) $^1$H NMR (D$_2$O) δ 3.36 (m, 1H, —C<u>H</u>CH$_2$NH$_2$), 3.10 (m, 2H, —C<u>H</u>$_2$NH$_2$), 1.37-1.58 (m, 6H), 1.28 (m, 1H), 0.91 (m, 3H), 0.69 (m, 3H). LRMS: m/z 208.2 (M−1). Anal. Calcd for C$_{10}$H$_{19}$N$_5$: C, 57.39; H, 9.15; N, 33.46. Found: C, 56.62; H, 9.09; N, 32.79.

Example 16

5-(4-Tert-butyl-phenyl)-4-methyl-2-(1H-tetrazol-5-yl)-pentylamine

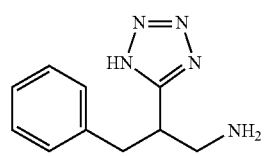

3:1 mixture of diastereomers by $^1$H NMR. LRMS: m/z 300.2 (M−1). Anal. Calcd for C$_{17}$H$_{27}$N$_5$: C, 67.74; H, 9.03; N, 23.23. Found: C, 66.68; H, 8.97; N, 22.84.

Example 17

3-Phenyl-2-(1H-tetrazol-5-yl)-propylamine $^1$H NMR (CD$_3$OD) δ 7.16 (m, 5H), 3.58 (m, 1H, —C<u>H</u>CH$_2$NH$_2$), 3.20 (m 3H, —C<u>H</u>$_2$NH$_2$, —CH<u>H</u>Ph), 2.96 (dd, J=13.7, 7.8 Hz, 1H, —C<u>H</u>HPh). LRMS: m/z202.1 (M−1).

Example 18

2-Cyclopentyl-2-(1H-tetrazol-5-yl)-ethylamine

A. Cyclopentylidene-(2-trityl-2h-tetrazol-5-yl)-acetonitrile

To a flask charged with dry sodium hydride (0.32 g, 13.3 mmol) was added (2-trityl-2H-tetrazol-5-yl)-acetonitrile (2.34 g, 6.67 mmol). The solids were swirled to mix, cooled to 0° C., and 25 mL THF was added quickly, resulting in vigorous $H_2$ evolution and a bright yellow foam. The mixture was stirred at 0° C. for 5 min, at which time the ice bath was removed and stirring continued for 10 min. Cyclopentanone (0.65 mL, 7.33 mmol) in 10 mL THF was added quickly resulting in a clear orange solution. The mixture was stirred for 2 h, partitioned between EtOAc and sat. $NH_4Cl$ (aq), and the organic phase dried ($MgSO_4$) and concentrated. Flash chromatography of the residue ($CH_2Cl_2$) furnished 2.05 g (74%) of cyclopentylidene-(2-trityl-2H-tetrazol-5-yl)-acetonitrile as a white solid. $^1H$ NMR ($CDCl_3$) δ 7.32 (m, 9H), 7.10 (m, 6H), 2.86 (m, 4H, —C$\underline{H}_2$CC$\underline{H}_2$—), 1.84 (m, 4H, —CH$_2$C$\underline{H}_2$C$\underline{H}_2$CH$_2$—).

B. 2-Cyclopentyl-2-(1H-tetrazol-5-yl)-ethylamine

To a solution of cyclopentylidene-(2-trityl-2H-tetrazol-5-yl)-acetonitrile (2.05 g, 4.91 mmol) in 50 mL MeOH:THF (1:1) was added $PtO_2$ (0.2 g), concentrated HCl (1.49 g), and the mixture was hydrogenated in a Parr shaker at 48 psi for 8 h. The mixture was filtered and concentrated. Flash chromatography of the residue on silica gel (0.25:1.25:3.5 conc. $NH_4OH$ (aq):MeOH:$CH_2Cl_2$), followed by a second column using the same conditions, provided 0.54 g (61%) of 2-cyclopentyl-2-(1H-tetrazol-5-yl)-ethylamine as a colorless solid. $^1H$ NMR ($D_2O$) δ 3.22 (m, 2H, —C$\underline{H}_2$NH$_2$), 3.06 (m, 1H, —C$\underline{H}$CH$_2$NH$_2$), 1.99 (m, 1H, —C$\underline{H}$CHCH$_2$NH$_2$), 1.72 (m, 1H), 1.03-1.38 (m, 6H), 0.87 (m, 1H). $^{13}C$ NMR ($CD_3OD$) □ 161.11, 42.78, 42.56, 40.48, 30.61, 30.11, 24.96, 24.53. LRMS: m/z 180.1 (M−1). Anal. Calc'd for $C_8H_{15}N_5$: C, 53.02; H, 8.34; N, 38.64. Found: C, 51.59; H, 8.18; N, 37.96.

The title compounds of Example 19 through Example 28 were prepared according to procedures analogous to those described in Example 18.

Example 19

2-Cyclohexyl-2-(1H-tetrazol-5-yl)-ethylamine

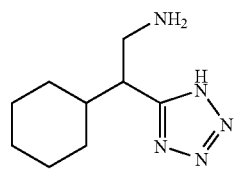

LRMS: m/z 194.1 (M−1). Anal. Calcd for $C_9H_{17}N_5$: C, 55.36; H, 8.78; N, 35.87. Found: C, 55.06; H, 8.71; N, 35.39.

Example 20

2-(3,5-Dimethyl-cyclohexyl)-2-(1H-tetrazol-5-yl)-ethylamine

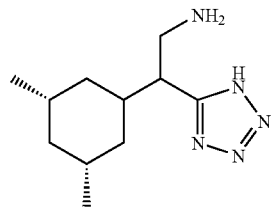

1:1:1:1 mixture of diastereomers after HPLC analysis of the corresponding Marfey's derivative. LRMS: m/z 222.2 (M−1).

Example 21

2-Cycloheptyl-2-(1H-tetrazol-5-yl)-ethylamine

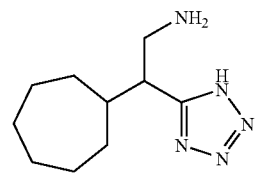

$^1H$ NMR ($D_2O$) δ 3.25 (d, J=7.6 Hz, 2H, —C$\underline{H}_2$NH$_2$), 3.12 (m, 1H, —C$\underline{H}$CH$_2$NH$_2$), 1.76 (m, 1H, —C$\underline{H}$CHCH$_2$NH$_2$), 1.53 (m, 1H), 1.06-1.33 (m, 10H), 0.94 (m, 1H). LRMS: m/z 208.2 (M−1).

Example 22

3,4-Dimethyl-2-(1H-tetrazol-5-yl)-pentylamine

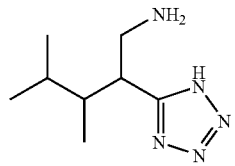

mp>250° C. (dec). $^1H$ NMR ($CD_3OD$) δ 3.32 (m, 3H, —C$\underline{H}_2$NH$_2$, —C$\underline{H}$CH$_2$NH$_2$), 1.82 (m, 1H, —CH[C$\underline{H}_3$]$_2$), 1.25 (m, 1H, —C$\underline{H}$CH$_3$), (1.00 (d, J=6.4 Hz, 3H, —C$\underline{H}_3$), 0.92 (d, J=6.8 Hz, 3H, —C$\underline{H}_3$), 0.87 (d, J=7.1 Hz, 3H, —C$\underline{H}_3$), 0.82 (d, J=6.6 Hz, 3H, —C$\underline{H}_3$), 0.79 (d, J=6.6 Hz, 3H, —C$\underline{H}_3$), 0.64 (d, J=6.6 Hz, 3H, —C$\underline{H}_3$) (diastereomeric mixture). LRMS: m/z 184.1 (M+1). HRMS: [M+H]+Calcd for $C_8H_{17}N_5$: 184.1562. Found: 184.1563.

Example 23

3-Ethyl-4-methyl-2-(1H-tetrazol-5-yl)-pentylamine

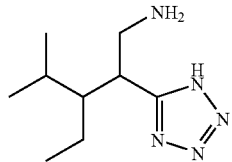

mp 205° C. (dec). $^1$H NMR (CD$_3$OD) δ 3.42 (m, 2H, —CH$_2$NH$_2$), 3.14 (m, 1H, —CHCH$_2$NH$_2$), 1.81 (m, 1H, —CH[CH$_3$]$_2$), 1.56 (m, 2H, —CHCH$_2$CH$_3$), 1.37 (m, —CH$_2$CH$_3$), (0.90 (m, 3H, —CH$_3$), 0.80 (m, 3H, —CH$_3$), 0.66 (m, 3H, —CH$_3$) (diastereomeric mixture). LRMS: m/z 198.1 (M+1). HRMS: [M+H]+Calcd for C$_9$H$_{17}$N$_5$: 198.1718. Found: 198.1713.

Example 24

4-Cyclopentyl-3-methyl-2-(1H-tetrazol-5-yl)-butylamine

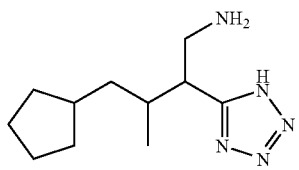

mp 194° C. (dec). $^1$H NMR (CD$_3$OD) δ 3.41 (m, 2H, —CH$_2$NH$_2$), 3.18 (m, 1H, —CHCH$_2$NH$_2$), 1.98 (m, 1H, —CHHCH<), 1.84 (m, 1H —CHHCH<), 1.74 (m, 2H —CH$_2$CH<), 1.54 (m, 4H, —CH$_2$CH$_2$—), 1.29 (m, —CH$_2$CH[CH$_2$—]), 1.19 (m, 1H, CH$_3$CH—), 1.03 (m, 2H, >CHCH$_2$—), 0.90 (d, J=6.8 Hz, 3H, —CH$_3$ (diastereomer 1)), 0.83 (d, J=6.8 Hz, 3H, —CH$_3$ (diastereomer 2)). LRMS: m/z 224.2 (M+1). HRMS: [M+H]+Calcd for C$_{11}$H$_{21}$N$_5$: 224.1875. Found: 224.1869.

Example 25

4-Cyclohexyl-3-methyl-2-(1H-tetrazol-5-yl)-butylamine

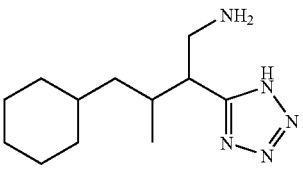

mp 216° C. (dec). $^1$H NMR (CD$_3$OD) δ 3.42 (m, 1H, —CH$_2$NH$_2$), 3.16 (m, 1H, —CHCH$_2$NH$_2$), 2.06 (m, 1H, —CH$_2$CH[CH$_2$—]), 1.65 (m, 6H, —CH$_2$—), 1.18 (m, 6H, —CH$_2$—), 0.96 (m, 1H, CH$_3$CH—), 0.87 (d, J=6.8 Hz, 3H, CH$_3$— (diastereomer 2)). LRMS: m/z 238.2 (M+1). HRMS: [M+H]+Calcd for C$_{12}$H$_{23}$N$_5$: 238.2031. Found: 238.2035.

Example 26

4-(4-Fluoro-phenyl)-3-methyl-2-(1H-tetrazol-5-yl)-butylamine

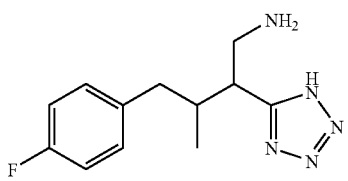

mp 186° C. (dec). $^1$H NMR (CD$_3$OD) δ 7.15 (m, 2H, Ar—H, 6.96 (dt, J$_1$=8.8 Hz, J$_2$=2.2 Hz, 2H, Ar—H, 3.40 (m, 3H, —CH$_2$NH$_2$, —CHCH$_2$NH$_2$), 2.77 (dd, J$_1$=12.8 Hz, J$_2$=4.5 Hz, 1H, Ar—CH$_9$—), 2.60 (m, 1H, Ar—CH$_2$—), 2.22 (m, 1H, —CH$_2$CH$_3$), 0.83 (d, J=6.5 Hz, 3H, CH$_3$— (diastereomer 1)), 0.72 (d, J=6.5 Hz, 3H, CH$_3$— (diastereomer 2)). LRMS: m/z 250.1 (M+1). HRMS: [M+H]+Calcd for C$_{12}$H$_{16}$FN$_5$: 250.1468. Found: 250.1468.

Example 27

3-Methyl-2-(1H-tetrazol-5-yl)-4-(3-trifluoromethyl-phenyl)-butylamine

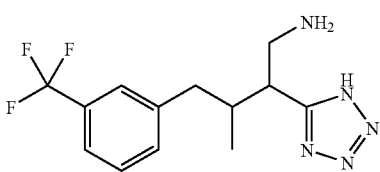

mp 163° C. (dec). $^1$H NMR (CD$_3$OD) δ 7.40 (m, 4H, Ar—H), 2.77 (m, 2H, Ar—CH$_2$—), 2.30 (m, 1H, —CHCH$_3$), 0.84 (d, J=6.5 Hz, 3H, CH$_3$— (diastereomer 1)), 0.73 (d, J=6.5 Hz, 3H, CH$_3$— (diastereomer 2)). LRMS: m/z 300.1 (M+1).

HRMS: [M+H]+Calcd for C$_{13}$H$_{16}$F$_3$N$_5$: 300.1436. Found: 300.1432.

Example 28

3-Methyl-5-phenyl-2-(1H-tetrazol-5-yl)-pentylamine

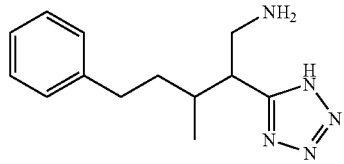

mp 152° C. (dec). $^1$H NMR (CD$_3$OD) δ 7.20 (m, 2H, Ar—H), 7.11 (m, 3H, Ar—H), 3.42 (m, 1H, —CHHNH$_2$), 2.63 (m, 3H, —CH$_2$NH$_2$, ArCH$_2$—), 2.46 (m, 1H, —CHCH$_2$NH$_2$), 1.95 (m, 1H, ArCH$_2$CHH—), 1.65 (m, 1H, CH$_3$CH—), 1.34 (m, 1H ArCH$_2$CHH—), 1.00 (d, J=6.8 Hz, 3H, CH$_3$— (diastereomer 1)), 0.88 (d, J=6.8 Hz, 3H, CH$_3$— (diastereomer 2)). LRMS: m/z 246.2 (M+1). HRMS: [M+H]+Calcd for C$_{13}$H$_{19}$N$_5$: 246.1718. Found: 246.1715.

Example 29

C-[2-Cyclohexyl-1-(1H-tetrazol-5-yl)-cyclopropyl]-methylamine

A. (4S)-Methyl-2-(2-trityl-2H-tetrazol-5-yl)-hexanenitrile

To a flask charged with dry sodium hydride (0.06 g, 2.54 mmol) was added (2-trityl-2H-tetrazol-5-yl)-acetonitrile (0.45 g, 1.27 mmol). The solids were swirled to mix, cooled to 0° C., and 5 mL THF was added quickly, resulting in Vigorous $H_2$ evolution and a bright yellow foam. The mixture was stirred at 0° C. for 5 min, at which time the ice bath was removed and stirring continued for 1 h. (S)-(+)-1-bromo-2-methylbutane (0.17 mL, 1.40 mmol) in 1 mL THF was added quickly and the mixture stirred overnight. The mixture was partitioned between EtOAc and sat. $NH_4Cl$ (aq), and the organic phase dried ($MgSO_4$) and concentrated. Flash chromatography of the residue (10% EtOAc/hexanes) furnished 0.33 g of (4S)-methyl-2-(2-trityl-2H-tetrazol-5-yl)-hexanenitrile contaminated with starting alkyl bromide as a light pink oil.

B. (4S)-Methyl-2-(1H-tetrazol-5-yl)-hexylamine

To a solution of (4S)-methyl-2-(2-trityl-2H-tetrazol-5-yl)-hexanenitrile (0.33 g, conta minated with [+]-1-bromo-2-methylbutane) in 16 mL MeOH was added $PtO_2$ (50 mg), concentrated HCl (0.24 g), and the mixture was hydrogenated in a Parr shaker at 48 psi for 60H. The mixture was filtered and concentrated. Flash chromatography of the residue on silica gel (0.25:1.25:3.5 conc. $NH_4OH$ (aq):MeOH:$CH_2Cl_2$) afforded 0.037 g. (16%, two steps) of (4S)-methyl-2-(1H-tetrazol-5-yl)-hexylamine as a colorless solid. $^1H$ NMR ($D_2O$): 1:1 Mixture of two diastereomers, salient peaks δ 3.32 (m, 1H, —C$\underline{H}$CH$_2$NH$_2$), 3.11 (m, —C$\underline{H}_2$NH$_2$). LRMS: m/z 182.1 (M–1).

C. 2-Cyclohexyl-1-(2-trityl-2H-tetrazol-5-yl)-cylopropanecarbonitrile

To a solution of (2-trityl-2H-tetrazol-5-yl)-acetonitrile (1.0 g, 2.85 mmol) in 15 mL benzene was added cyclohexanecarboxaldehyde (0.38 mL, 3.13 mmol), 10 mL 10% NaOH (aq), and tetrabutylammonium bromide (50 mg). The mixture was stirred for 1 h, then poured into EtOAc. The phases were separated, and the organic phase dried ($MgSO_4$) and concentrated. Meanwhile, to trimethylsulfoxonium iodide (0.75 g, 3.42 mmol) in 7.0 mL DMF was added sodium hydride (60% dispersion in mineral oil, 0.14 g, 3.42 mmol). The mixture was stirred for 30 min at which time a solution of crude 3-cyclohexyl-2-(2-trityl-2H-tetrazol-5-yl)-acrylonitrile 2 (ca. 2.8 mmol) in 5.0 mL DMF was added quickly dropwise. The orange solution was stirred overnight, partitioned between EtOAc and $H_2O$, and the phases separated. The organic phase was washed with brine, dried ($MgSO_4$) and concentrated. Flash chromatography of the residue (15→20% EtOAc/hexanes) provided 1.15 g (88%, two steps) of 2-cyclohexyl-1-(2-trityl-2H-tetrazol-5-yl)-cyclopropanecarbonitrile as a colorless foam. $^1H$ NMR (CDCl$_3$) δ 7.33 (m, 9H), 7.07 (m, 6H), 1.88 (dd, J=4.9, 8.8 Hz, 1H, cyclopropyl —C$\underline{H}$H), 1.66-1.84 (m, 4H), 1.57 (dd, J=4.9, 7.7 Hz, 1H, cyclopropyl —CH$\underline{H}$), 1.25 (m, 8H).

D. C-[2-Cyclohexyl-1-(1H-tetrazol-5-yl)-cyclopropyl]-methylamine

To a solution of the 2-cyclohexyl-1-(2-trityl-2H-tetrazol-5-yl)-cyclopropanecarbonitrile (1.10 g, 2.39 mmol) in 50 mL 2.0M $NH_3$ in EtOH was added RaNi (1.4 g), and the mixture was hydrogenated in a Parr shaker at 48 psi for 60 h. The mixture was filtered and concentrated. Flash chromatography of the residue on silica gel (0.25:1.25:3.5 conc. $NH_4OH$ (aq):MeOH:$CH_2Cl_2$) furnished 0.19 g (36%) of C-[2-cyclohexyl-1-(1H-tetrazol-5-yl)-cyclopropyl]-methylamine as a colorless solid. $^1H$ NMR (CD$_3$OD) δ 3.97 (d, J=13.2 Hz, 1H, —C$\underline{H}_2$NH$_2$), 2.96 (d, J=13.2 Hz, 1H, —C$\underline{H}_2$NH$_2$), 1.87 (m, 1H), 1.77 (m, 1H), 1.68 (m, 2H), 1.47 (m, 1H), 1.38 (m, 1H), 1.12-1.31 (m, 6H), 1.07 (m, 1H), 0.91 (dd, J=4.6, 6.6 Hz, 1H, cyclopropyl —CH$\underline{H}$). LRMS: m/z 220.2 (M–1). Anal. Calc'd for $C_{11}H_{19}N_5$: C, 59.70; H, 8.65; N, 31.65. Found: C, 58.39; H, 8.54; N, 31.20.

The title compounds of Examples 30 and 31 were prepared according to procedures analogous to those described in Example 29.

Example 30

C-[2-Isopropyl-1-(1H-tetrazol-5-yl)-cyclopropyl]-methylamine

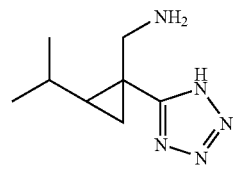

mp>250° C. (dec). $^1H$ NMR (D$_2$O) δ 3.88 (d, J=13.4 Hz, 1H), 2.97 (d, J=13.4 Hz, 1H), 1.38 (m, 1H), 1.20 (m, 1H), 1.06 (m, 1H), 0.90 (d, J=6.6 Hz, 3H), 0.84 (m, 1H), 0.81 (d, J=6.6 Hz, 3H). LRMS: m/z 180.1 (M–1). 1D $^1H$ NMR and 2D NOESY & COSY data were used to determine that the isopropyl and aminomethyl groups resided cis to each other on the cyclopropane ring.

Example 31

C-[2-(1-Ethyl-propyl)-1-(1H-tetrazol-5-yl)-cyclopropyl]-methylamine

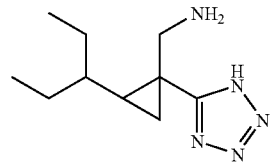

mp>250° C. (dec). $^1H$ NMR (CD$_3$OD) δ 3.97 (d, J=13.2 Hz, 1H), 2.88 (d, J=13.2 Hz, 1H), 1.29-1.56 (m, 6H), 1.05 (m, 1H), 0.97 (t, J=7.6 Hz, 3H), 0.94 (m, 1H), 0.83 (t, J=7.6 Hz, 3H). LRMS: m/z 208.2(M–1).

Example 32

C-[1-(1H-Tetrazol-5-yl)-spiro[2.5]oct-1-yl]-methylamine

A. 1-(2-Trityl-2H-tetrazol-5-yl)-spiro[2.5]octane-1-carbonitrile

To a flask charged with dry sodium hydride (0.34 g, 14.1 mmol) was added (2-trityl-2H-tetrazol-5-yl)-acetonitrile (2.49 g, 7.10 mmol). The solids were swirled to mix, cooled to 0° C., and 25 mL THF was added quickly, resulting in vigorous $H_2$ evolution and a bright yellow foam. The mixture was stirred at 0° C. for 5 min, at which time the ice bath was removed and stirring continued for 10 min. Cyclohexanone (0.81 mL, 7.80 mmol) in 10 mL THF was added quickly resulting in a clear orange solution. The mixture was stirred for 2 h, partitioned between EtOAc and sat. $NH_4Cl$ (aq), and the organic phase dried ($MgSO_4$) and concentrated. Meanwhile, to trimethylsulfoxonium iodide (2.48 g, 11.2 mmol) in 25 mL DMF was added sodium hydride (60% dispersion in mineral oil, 0.45 g, 11.2 mmol). The mixture was stirred for 30 min at which time a suspension of crude cyclohexylidene-(2-trityl-2H-tetrazol-5-yl)-acetonitrile (ca. 7.5 mmol) in 15 mL DMF was added quickly dropwise. The orange solution was stirred overnight, partitioned between EtOAc and $H_2O$, and the phases separated. The organic phase was washed with brine, dried ($MgSO_4$) and concentrated. Flash chromatography of the residue ($CH_2Cl_2$) provided 2.43 g (77%, two steps) of 1-(2-trityl-2H-tetrazol-5-yl)-spiro[2.5]octane-1-carbonitrile as a colorless foam. $^1H$ NMR ($CDCl_3$) δ 7.32 (m, 9H), 7.08 (m, 6H), 1.99 (d, J=5.4 Hz, 1H, cyclopropyl —CHH), 1.80 (m, 2H), 1.72 (m, 2H), 1.59 (d, J=5.4 Hz, 1H, cyclopropyl —CHH), 1.51 (m, 1H), 1.41 (m, 1H), 1.29 (m, 3H), 1.09 (m, 2H), 0.83 (m, 1H).

B. C-[1-(1H-Tetrazol-5-yl)-spiro[2.5]oct-1-yl]-methylamine

To a solution of the 1-(2-trityl-2H-tetrazol-5-yl)-spiro[2.5]octane-1-carbonitrile (2.40 g, 2.39 mmol) in 100 mL MeOH:THF (1:1) was added $PtO_2$ (0.15 g), concentrated HCl (1.67 g), and the mixture was hydrogenated in a Parr shaker at 48 psi for 20 h. The mixture was filtered and concentrated. Flash chromatography of the residue on silica gel (0.25:1.25:3.5 conc. $NH_4OH$ (aq):MeOH:$CH_2Cl_2$) furnished 0.40 g (36%) of C-[1-(1H-tetrazol-5-yl)-spiro[2.5]oct-1-yl]-methylamine as a colorless solid. $^1H$ NMR ($CD_3OD$) δ 3.77 (d, J=13.2 Hz, 1H, —CH$_2$H$_2$), 3.07 (d, J=13.2 Hz, 1H, —CH$_2$H$_2$), 1.66 (m, 1H), 1.53 (d, J=5.1 Hz, 1H, cyclopropyl —CHH), 1.47-1.59 (m, 4H), 1.22-1.42 (m, 3H), 1.06 (m, 1H), 0.97 (m, 1H), 0.88 (d, J=5.1 Hz, 1H, cyclopropyl —CHH). $^{13}C$ NMR ($CD_3OD$) δ 161.18, 31.61, 31.51, 26.00, 25.76, 25.30, 24.78, 21.67. LRMS: m/z 206.1 (M−1). Anal. Calc'd for $C_{10}H_{17}N_5$: C, 57.95; H, 8.27; N, 33.79. Found: C, 56.83; H, 8.24; N, 33.40.

Example 33

1-Aminomethyl-spiro[2.4]heptane-1-carboxylic acid

A. Cyano-cyclopentylidene-acetic acid methyl ester

To a solution of cyclopentanone (84.1 g, 1 mol) in dry benzene (100 mL) was added methyl cyanoacetate (99.1 g, 1 mol), ammonium acetate (10 g) and glacial acetic acid (20 mL). The reaction mixture was heated to reflux using Dean-Stark apparatus for 12 hours and allowed to cool to room temperature. Excess of solvents was removed in vacuo and the residue was dissolved in EtOAc (400 mL). The organic layer was washed with water, dried ($Na_2SO_4$) and evaporated to give the product as pale yellow oil. Further purification of the pale yellow oil by distillation (10 mm Hg, 140-145° C.) provided cyano-cyclopentylidene-acetic acid methyl ester (130 g, 79%) as a colorless oil: $^1H$ NMR (300 MHz, $CDCl_3$) δ 1.80 (m, 4H), 2.80 (t, 2H), 3.0 (t, 2H), 3.80 (s, 3H); $^{13}C$ NMR (75 MHz, $CDCl_3$) δ 25.4, 26.9, 35.8, 38.1, 52.5, 100.7, 115.8, 162.6, 188.3.

B. 1-Cyano-spiro[2.4]heptane-1-carboxylic acid methyl ester

To a solution of cyano-cyclopentylidene-acetic acid methyl ester (20.8 g, 126 mmol), in acetonitrile (500 mL) was added nitromethane (34 mL, 630 mmol, 5 eq) followed by dropwise addition of 1,8-diazabicyclo[5.4.0]undec-7-ene (DBU) (18.8 mL, 126 mmol). The reaction solution turned orange upon the addition of DBU. The reaction mixture was stirred at room temperature for 16 hours. Another portion of DBU (1 mL) was added and stirred for 1 hour. The reaction mixture was partitioned between ether (1 L) and 1N HCl (400 mL) and the layers separated. The organic layer was washed with 1N HCl (2×300 mL), brine (2×200 mL), dried over sodium sulfate, filtered and evaporated. The residue was chromatographed on a wet-packed silica gel column eluting with 4-6% ethyl acetate/hexanes. The appropriate fractions were combined and evaporated to furnish 14.0 g (62%) of 1-cyano-spiro[2.4]heptane-1-carboxylic acid methyl ester as a clear oil: $^1H$ NMR (300 MHz, $CDCl_3$) δ 1.64 (d, J=5.0 Hz, 1H), 1.70-1.88 (m, 7H), 2.14 (d, J=5.0 Hz, 1H), 2.1-2.19 (m, 1H), 3.82 (s, 3H); MS (APCI) m/z 180 $[M+H]^+$.

C. 1-Aminomethyl-spiro[2.4]heptane-1-carboxylic acid methyl ester

To a solution of 1-cyano-spiro[2.4]heptane-1-carboxylic acid methyl ester (3.45 g, 19.3 mmol) in methanol (240 mL) was added $CoCl_2$-$6H_2O$ (9.16 g, 38.5 mmol) to give a deep purple colored solution. Sodium borohydride (7.30 g, 193 mmol) was added portionwise over 10 minutes with caution to control the evolution of hydrogen and the exothermic reaction that ensued to give a black solution. The reaction mixture was stirred for 30 minutes under nitrogen after the addition was completed. The reaction was quenched carefully by the addition of 0.5N HCl (1.3 L). The solution was made alkaline (pH~9) by the addition of concentrated ammonium hydroxide. The mixture was extracted with ethyl acetate (4×400 mL). The combined organic layers were dried over sodium sulfate, filtered and evaporated to afford 3.07 g (87%) of 1-aminomethyl-spiro[2.4]heptane-1-carboxylic acid methyl ester as a yellow oil: $^1H$ NMR (300 MHz, $CDCl_3$) δ 0.74 (br d, 1H), 1.4-1.7 (m, 10H), 1.9 (m, 1H), 2.58 (d, J=13.8 Hz, 1H), 3.16 (d, J=13.8 Hz, 1H), 3.48 (s, 3H); MS (APCI) m/z 184 $[M+H]^+$.

D. 1-Aminomethyl-spiro[2.4]heptane-1-carboxylic acid

To a solution of 1-aminomethyl-spiro[2.4]heptane-1-carboxylic acid methyl ester (3.40 g, 18.6 mmol) was added methanol (75 mL) and LiOH—$H_2O$ (1.55 g, 37.1 mmol). The mixture was heated to reflux under nitrogen for 48 hours. The solvent was removed by evaporation under reduced pressure and the residue was dissolved in water (50 mL). With ice bath cooling, concentrated HCl (~2.5 mL) was added until the pH was adjusted to 6. A white precipitate was isolated by filtration and dried under vacuum to yield 1.22 g (39%) of 1-aminomethyl-spiro[2.4]heptane-1-carboxylic acid as an off-white solid: mp 231-235° C. (decomposition); $^1H$ NMR (300 MHz, $D_2O$) δ 0.78 (d, J=4.7 Hz, 1H), 1.32 (d, J=4.7 Hz, 1H), 1.40 (m, 1H), 1.54-1.77 (m, 7H), 2.86 (d, J=13.2 Hz, 1H), 3.43 (d, J=13.2 Hz, 1H); MS (APCI) m/z 170 $[M+H]^+$. Anal. Calcd. For $C_9H_{15}NO_2$-1.1$H_2O$: C, 57.18; H, 9.17; N, 7.41. Found: C, 57.38; H, 8.82; N, 7.09.

Example 34

3-(1-Aminomethyl-spiro[2.4]hept-1-yl)-4H-[1,2,4]oxadiazol-5-one hydrochloride A. Cyano-cyclohexylidene-acetic acid methyl ester To a solution of cyclohexanone (84.1 g, 1 mol) in dry benzene (100 mL) was added methyl cyanoacetate (99.1 g, 1 mol), ammonium acetate (10 g) and glacial acetic acid (20 mL). The reaction mixture was heated to reflux using Dean-Stark apparatus for 12 hours and allowed to cool to room temperature. Excess of solvents was removed in vacuo and the residue was dissolved in EtOAc (400 mL). The organic layer was washed with water, dried over sodium sulfate and evaporated to give cyano-cyclohexylidene-acetic acid methyl ester as pale yellow oil. Further purification of the pale yellow oil by distillation (10 mm Hg, 150-155° C.) gave product 15 (110 g, 61%) as a colorless oil: $^1$H NMR (300 MHz, CDCl$_3$) δ 1.70-1.85 (m, 6H), 2.70 (t, 2H), 3.00 (t, 2H), 3.80 (s, 3H); $^{13}$C NMR (75 MHz, CDCl$_3$) δ 25.9, 28.6, 28.9, 31.9, 37.2, 52.8, 101.9, 115.8, 162.7, 180.8.

B. 1-Cyano-spiro[2.5]octane-1-carboxylic acid methyl ester

To a solution of cyano-cyclohexylidene-acetic acid methyl ester (20.0 g, 112 mmol) in acetonitrile (400 mL) was added nitromethane (30 mL, 558 mmol) followed by dropwise addition of DBU (16.9 mL, 113 mmol) over five minutes. The solution went from clear to orange and was stirred at room temperature for 5.5 hours. The solution was diluted with ether (1 L), washed with 1N HCl (2×250 mL) and then brine (2×250 mL). The organic layer was dried over sodium sulfate, filtered and evaporated. The residue was chromatographed on a wet-packed silica gel column (6.5×40 cm) eluting with 95:5 hexanes/ethyl acetate. The appropriate fractions were combined and evaporated to give 18.6 g (86%) of 1-cyano-spiro[2.5]octane-1-carboxylic acid methyl ester as a clear oil: $^1$H NMR (300 MHz, CDCl$_3$) δ 1.35 (m, 1H), 1.49 (d, J=5.0 Hz, 1H), 1.5-1.75 (m, 9H), 1.82 (d, J=5.0 Hz, 1H), 3.83 (s, 3H).

C. 1-(tert-Butoxycarbonylamino-methyl)-spiro[2.5]octane-1-carboxylic acid methyl ester To a solution of 1-cyano-spiro[2.5]octane-1-carboxylic acid methyl ester (18.6 g, 96.2 mmol) in methanol (480 mL) was added CoCl$_2$—H$_2$O (22.8 g, 96.2 mmol) to give a deep purple color. Sodium borohydride (14.5 g, 385 mmol) was added portionwise over 10 minutes with ice bath cooling to give a black colored solution. After 40 minutes, the reaction was quenched carefully with 2N HCl. The pH was adjusted to 9 with 2N NaOH and the solution was extracted with CH$_2$Cl$_2$ (4 times). To the combined organic layer was added saturated potassium carbonate solution and di-tert-butyldicarbonate (26.2 g, 120 mmol). After 1 hour, the layers were separated. The organic layer was dried over sodium sulfate, filtered and evaporated to give 35.7 g (>100%) of 1-(tert-butoxycarbonylamino-methyl)-spiro[2.5]octane-1-carboxylic acid methyl ester as an off-white solid. The material was used without further purification in the next step.

D. 1-(tert-Butoxycarbonylamino-methyl)-spiro[2.5]octane-1-carboxylic acid

To a solution of crude 1-(tert-butoxycarbonylamino-methyl)-spiro[2.5]octane-1-carboxylic acid methyl ester (35.0 g, ~96.2 mmol) was added LiOH—H$_2$O (12.3 g, 294 mmol) followed by the addition of water (75 mL). The mixture was heated to reflux. After 48 hours, an additional portion of LiOH—H$_2$O (6.15 g, 146 mmol) was added and refluxed for an additional 24 hours. The solvent was removed under reduced vacuum. The residue was partitioned between water and ether. The aqueous layer was acidified to pH 2-3 with aqueous HCl with ice bath cooling with a layer of CH$_2$Cl$_2$ present. The layers were separated and the aqueous layer was extracted with CH$_2$Cl$_2$ (3 times). The combined organic layers were dried over sodium sulfate, filtered and evaporated to give 17.0 g (63%, 2 steps) of 1-(tert-butoxycarbonylamino-methyl)-spiro[2.5]octane-1-carboxylic acid an off-white solid.

E. 1-Aminomethyl-spiro[2.5]octane-1-carboxylic acid hydrochloride

To a solution of 1-(tert-butoxycarbonylamino-methyl)-spiro[2.5]octane-1-carboxylic acid (200 mg, 0.706 mmol) in 1,4-dioxane (3 mL) was added 4N HCl in 1,4-dioxane (3 mL). The reaction was stirred for 18 hours at room temperature. Ether (20 mL) was added and the precipitate was isolated by vacuum filtration. The solid was dried in a vacuum oven at 48° C. to give 133 mg (86%) of 1-aminomethyl-spiro[2.5]octane-1-carboxylic acid hydrochloride as a white solid: mp 240-242° C.; $^1$H NMR (300 MHz, D$_2$O) δ 0.92 (d, J=5.2 Hz, 1H), 1.40 (d, J=5.2 Hz, 1H), 1.4-1.6 (m, 10H), 3.12 (d, J=14.0 Hz, 0.1H), 3.61 (d, J=14.0 Hz, 1H); MS (APCI) m/z 184 [M+H]$^+$. Anal. Calc'd For C$_{10}$H$_{17}$NO$_2$—HCl: C, 54.67; H, 8.26; N, 6.38; Cl, 16.14. Found: C, 54.91; H, 8.36; N, 6.25; Cl, 15.99.

F. 1-(tert-Butoxycarbonylaminomethyl)-spiro[2.4]heptane-1-carboxylic acid methyl ester To a solution of 1-cyano-spiro[2.4]heptane-1-carboxylic acid methyl ester (14.0 g, 78.1 mmol) in methanol (275 mL) was added CoCl$_2$-6H$_2$O (10.6 g, 44.6 mmol) to give a deep purple colored solution. Sodium borohydride (8.44 g, 223 mmol) was added portionwise over 10 minutes with caution to control the evolution of hydrogen and the exothermic reaction that ensued to give a black solution. The reaction mixture was stirred for 30 minutes under nitrogen after the addition was completed. The reaction was quenched carefully by the addition of 1N HCl (300 mL). A saturated potassium carbonate solution was added until pH=9. Di-tert-butyl dicarbonate (21.3 g, 97.6 mmol) in CH$_2$Cl$_2$ (250 mL) and was added and stirred for 2 hours. The layers were separated and the aqueous layer was extracted with CH$_2$Cl$_2$. The combined organic layers were dried over sodium sulfate, filtered and evaporated. The residue was chromotographed on a wet-packed silica gel column (6.5×26 cm) using 90:10 hexanes/ethyl acetate as eluent. The appropriate fractions were combined and evaporated to give 16.6 g (75%) of 1-(tert-butoxycarbonylaminomethyl)-spiro[2.4]heptane-1-carboxylic acid methyl ester as a thick oil: $^1$H NMR (300 MHz, CDCl$_3$) δ 0.95 (d, J=4.3 Hz, 1H), 1.44 (s, 9H), 1.45 (m, 2H), 1.60-1.75 (m, 6H), 1.90 (m, 1H), 3.30 (dd, J=6.0, 14.0 Hz, 1H), 3.47 (dd, J=6.0, 14.0 Hz, 1H), 3.70 (s, 3H), 5.16 (brs, 1H); MS (APCI) m/z 184 [M+H-100 (Boc)]$^+$.

G. 1-(tert-Butoxycarbonylaminomethyl)-spiro[2.4]heptane-1-carboxylic acid

To a solution of 1-(tert-butoxycarbonylaminomethyl)-spiro[2.4]heptane-1-carboxylic acid methyl ester (16.5 g, 58.2 mmol) in methanol (100 mL) was added LiOH—H$_2$O (4.9 g, 116 mmol) and water (15 mL). After 3 hours, additional methanol (50 mL) and water (15 mL) was added and reflux was continued for 6 hours total. The solvent was removed under reduced pressure. The residue was dissolved in water (200 mL) and washed with ether (200 mL). The aqueous solution was cooled in an ice bath and methylene chloride (200 mL) was added. With stirring, 4N HCl was added dropwise until pH=2-3. The layers were separated and the aqueous layer was extracted with methylene chloride (2×300 mL). The combined organic layers were dried over sodium sulfate, filtered and evaporated. The residue was dissolved in hexane and evaporated to give 12.6 g (80%) of 1-(tert-butoxycarbonylaminomethyl)-spiro[2.4]heptane-1-carboxylic acid as a white foamy solid: $^1$H NMR (300 MHz, CDCl$_3$) δ 1.08 (d, J=5.0 Hz, 1H), 1.44 (s, 9H), 1.45 (m, 2H), 1.55-1.8 (m, 6H), 1.92 (m, 1H), 3.35 (dd, J=6.0, 14.0 Hz, 1H), 3.44 (dd, J=6.0, 14.0 Hz, 1H), 5.28 (br t, 1H); MS (APCI) m/z=170 [M+H-100(Boc)]$^+$.

H. (1-Carbamoyl-spiro[2.4]hept-1-ylmethyl)-carbamic acid tert-butyl ester

To a solution of 1-(tert-butoxycarbonylaminomethyl)-spiro[2.4]heptane-1-carboxylic acid (12.5 g, 46.6 mmol) in THF (450 mL) was added HOBT (6.6 g, 48.9 mmol), 4-methylmorpholine (5.4 mL, 48.9 mmol) and EDC (9.83 g, 51.3 mmol). The reaction mixtured was stirred for 3 hours and then concentrated aqueous ammonium hydroxide (6.3 mL, 93.2 mmol) was added. The reaction mixture was stirred for 48 hours. The solvent was removed under reduced pressure and the residue was partitioned between ethyl acetate (500 mL) and half saturated potassium hydrogen sulfate solution. The layers were separated. The organic layer was washed with half saturated potassium hydrogen sulfate, saturated sodium bicarbonate, brine, dried over sodium sulfate, filtered and evaporated to give 9.7 g (78%) of (1-carbamoyl-spiro[2.4]hept-1-ylmethyl)-carbamic acid tert-butyl ester as a white solid: $^1$H NMR (300 MHz, CDCl$_3$) δ 0.74 (d, J=4.5 Hz, 1H), 1.38 (d, J=4.5 Hz, 1H), 1.44 (s, 9H), 1.6-1.8 (m, 7H), 1.83 (m, 1H), 3.15 (dd, J=5.1, 14.8 Hz, 1H), 3.65 (dd, J=5.1, 14.8 Hz, 1H), 5.0 (br s, 1H), 5.49 (br s, 1H), 6.45 (br s, 1H); MS (APCI) m/z 169 [M+H-100 (Boc)]$^+$.

I. (1-Cyano-spiro[2.4]hept-1-ylmethyl)-carbamic acid tert-butyl ester

To a solution of (1-carbamoyl-spiro[2.4]hept-1-ylmethyl)-carbamic acid tert-butyl ester (9.7 g, 36.1 mmol) in DMF (150 mL) was added cyanuric chloride (9.2 g, 50.5 mmol) with ice bath cooling. After 30 minutes, a white precipitate began to form. After 40 minutes, the mixture was poured onto an ice cooled solution of 0.5N NaOH (300 mL). The mixture was poured into a separatory funnel and extracted with ethyl acetate (3×300 mL). The combined organic layers were dried over sodium sulfate, filtered and evaporated to give 13.1 g of a yellow oil. The oil was chromatographed on a wet-packed silica gel column (4×28 cm) eluting with 9:1 hexanes/ethyl acetate. The appropriate fractions were combined and evaporated to give 8.1 g (90%) of (1-cyano-spiro[2.4]hept-1-ylmethyl)-carbamic acid tert-butyl ester as a white solid: $^1$H NMR (300 MHz, CDCl$_3$) δ 1.08 (d, J=5.1 Hz, 1H), 1.25 (d, J=5.1 Hz, 1H), 1.45 (s, 9H), 1.45-1.9 (m, 7H), 2.0 (m, 1H), 3.3 (m, 2H), 4.89 (s, 1H); MS (APCI) m/z 249 [M-H]$^-$.

J. [1-(N-Hydroxycarbamimidoyl)-spiro[2.4]hept-1-ylmethyl]-carbamic acid tert-butyl ester To a suspension of (1-cyano-spiro[2.4]hept-1-ylmethyl)-carbamic acid tert-butyl ester (8.0 g, 32.0 mmol) and hydroxylamine hydrochloride (11.1 g, 160 mmol) in ethanol (550 mL) was added finely ground potassium hydroxide (9.0 g, 160 mmol). The suspension was heated to reflux for 20 hours. The solvent was removed under reduced pressure. The residue was partitioned between methylene chloride and water. The aqueous layer was extracted with methylene chloride (3 times). The combined organic layers were dried over sodium sulfate, filtered and evaporated to give 8.6 g of a semi-solid. The residue was chromatographed on a wet-packed silica gel column (8×30 cm) eluting with 97:3 CH$_2$Cl$_2$/MeOH. The appropriate fractions were combined and evaporated to give 4.33 g (48%) of [1-(N-hydroxycarbamimidoyl)-spiro[2.4]hept-1-ylmethyl]-carbamic acid tert-butyl ester as a grey solid: $^1$H NMR (300 MHz, CDCl$_3$) δ 0.67 (d, J=4.8 Hz, 1H), 1.08 (d, J=4.8 Hz, 1H), 1.43 (s, 9H), 1.45-1.51 (m, 3H), 1.6-1.9 (m, 6H), 3.03 (dd, J=5.1, 13.8 Hz, 1H), 3.53 (dd, J=5.1, 13.8 Hz, 1H), 4.68 (s, 2H), 5.13 (s, 1H); MS (APCI) m/z 284 [M+H]$^+$.

K. [1-(5-Oxo-4,5-dihydro-[1,2,4]oxadiazol-3-yl)-spiro[2.4]hept-1-ylmethyl]-carbamic acid tert-butyl ester To a solution of [1-(N-hydroxycarbamimidoyl)-spiro[2.4]hept-1-ylmethyl]-carbamic acid tert-butyl ester (3.65 g, 12.9 mmol) in THF (20 mL) was added 1,1'-carbonyldiimidazole (3.13 g, 19.3 mmol) in THF (50 mL). The mixture was heated to reflux for 7 hours. The THF was removed under reduced pressure and the residue was partitioned between ether (75 mL) and 1N NaOH (40 mL). The layers were separated and the organic layer was extracted with 1N NaOH (3×40 mL). The combined aqueous layers were acidified with solid potassium hydrogen sulfate until pH=3. The aqueous layer was extracted with methylene chloride (3×125 mL) and the combined organic layers were dried over sodium sulfate, filtered and evaporated to give 3.55 g (89%) of an off-white solid. The residue was chromatographed on a wet-packed silica gel column (6.5×28 cm) eluting with 97:3 methylene chloride/methanol. The appropriate fractions were combined and evaporated to give 3.05 g (76%) of [1-(5-oxo-4,5-dihydro-[1,2,4]oxadiazol-3-yl)-spiro[2.4]hept-1-ylmethyl]-carbamic acid tert-butyl ester as a white solid: $^1$H NMR (300 MHz, CDCl$_3$) δ 0.95 (d, J=5.3 Hz, 1H), 1.44 (s, 9H), 1.4-1.58 (m, 3H), 1.6-1.8 (m, 5H), 1.91 (m, 1H), 3.18 (dd, 1H), 3.77 (dd, 1H), 5.01 (s, 1H), 10.67 (s, 1H); MS (APCI) m/z 308 [M-H]$^-$.

L. 3-(1-Aminomethyl-spiro[2.4]hept-1-yl)-4H-[1,2,4]oxadiazol-5-one hydrochloride To a solution of [1-(5-oxo-4,5-dihydro-[1,2,4]oxadiazol-3-yl)-spiro[2.4]hept-1-ylmethyl]-carbamic acid tert-butyl ester (3.05 g, 9.86 mmol) in 1,4-dioxane (60 mL) was added 4N HCl in 1,4-dioxane (90 mL). The solution was stirred at room temperature overnight. Ether (300 mL) was added and the resultant precipitate was isolated by vacuum filtration. The solid was washed with ether and dried overnight in a vacuum oven to give 2.38 g (97%) of 3-(1-aminomethyl-spiro[2.4]hept-1-yl)-4H-[1,2,4]oxadiazol-5-one hydrochloride as a white solid: mp 206-208° C.; $^1$H NMR (300 MHz, CD$_3$OD) δ 1.24 (d, J=5.7 Hz, 1H), 1.4-1.52 (m, 2H), 1.55-1.65 (m, 2H), 1.7-1.85 (m, 4H), 1.86-1.97 (m, 1H), 3.00 (d, J=13.9 Hz, 1H), 3.60 (d, J=13.9 Hz, 1H); MS (APCI) m/z 210 [M+H]$^+$. Anal. Calcd. For C$_{10}$H$_{15}$N$_3$O$_2$—HCl: C, 48.88; H, 6.56; N, 17.10; Cl, 14.43. Found: C, 48.73; H, 6.35; N, 16.89; Cl, 14.12.

Example 35

3-(1-Aminomethyl-spiro[2.5]oct-1-yl)-4H-[1,2,4]oxadiazol-5-one hydrochloride

A. (1-Carbamoyl-spiro[2.5]oct-1-ylmethyl)-carbamic acid tert-butyl ester

To a solution of 1-(tert-butoxycarbonylamino-methyl)-spiro[2.5]octane-1-carboxylic acid methyl ester (17.9 g, 63.2 mmol) in THF (700 mL) was added HOBT (9.00 g, 66.4 mmol), 4-methylmorpholine (7.3 mL, 66.4 mmol) followed by EDC (13.9 g, 72.7 mmol). The solution was stirred for 2 hours and then concentrated ammonium hydroxide (8.5 mL, 126 mmol) was added. The mixture was stirred for 18 hours and then the solvent was removed under reduced pressure. The residue was partitioned between ethyl acetate and half saturated potassium hydrogen sulfate. An emulsion occurred but the layers were separable. The organic layer was washed with half saturated potassium hydrogen sulfate (2 times) and brine. The organic layer was filtered to remove the emulsified solid. The organic layer was dried over sodium sulfate and filtered. Hexane was added to the filtrate to induce crystallization. The precipitate was isolated by vacuum filtration, washed with hexane and dried in a vacuum oven to give 16.2 g (91%) of (1-carbamoyl-spiro[2.5]oct-1-ylmethyl)-carbamic acid tert-butyl ester as a white solid: $^1$H NMR (300 MHz, CDCl$_3$) δ 0.65 (d, J=5.0 Hz, 1H), 1.17 (d, J=5.0 Hz, 1H), 1.43(s, 9H), 1.4-1.5 (m, 4H), 1.7-1.7 (m, 6H), 3.37 (dd, J=6.0, 14.0 Hz, 1H), 3.60 (dd, J=6.0, 14.0 Hz, 1H), 5.0 (s, 1H), 5.38 (s, 1H), 6.1 (s, 1H); MS (APCI) m/z 283 [M+H]$^+$.

B. (1-Cyano-spiro[2.5]oct-1-ylmethyl)-carbamic acid tert-butyl ester (1-carbamoyl-spiro[2.5]oct-1-ylmethyl)-carbamic acid tert-butyl ester (13.1 g, 46.4 mmol) was suspended in DMF (400 mL) and cooled in an ice bath. Cyanuric chloride (11.8 g, 64.9 mmol) was added. After 20 minutes the solution was homogeneous and after 30 minutes a new precipitate began to form. After 1 hour, the mixture was poured over 0.5N NaOH (500 mL) with ice bath cooling and then transferred to a separatory funnel. The solution was extracted with ethyl acetate (3×400 mL). The combined organic layers were washed with brine (2×400 mL), dried over sodium sulfate, filtered and evaporated under reduced pressure. The residue was dissolved in ethyl acetate (300 mL), washed with brine (3×300 mL), dried over sodium sulfate, filtered and evaporated to give 12.1 g (98%) of (1-cyano-spiro[2.5]oct-1-ylmethyl)-carbamic acid tert-butyl ester as an off-white solid: $^1$H NMR (300 MHz, CDCl$_3$) δ 0.96 (d, J=5.2 Hz, 1H), 1.07 (d, J=5.2 Hz, 1H), 1.46 (s, 9H), 1.4-1.7 (m, 10H), 3.40 (m, 2H), 4.95 (s, 1H); MS (APCI) m/z 263 [M–H]$^-$.

C. [1-(N-Hydroxycarbamimidoyl)-spiro[2.5]oct-1-ylmethyl]-carbamic acid tert-butyl ester To a solution of (1-cyano-spiro[2.5]oct-1-ylmethyl)-carbamic acid tert-butyl ester (10.0 g, 37.8 mmol) in ethanol (150 mL) was added 50% aqueous hydroxylamine (12 mL, 189 mmol). The solution was heated to reflux for 14 hours, cooled to room temperature and the solvent removed under reduced vacuum. The residue was partitioned between water (200 mL) and ether (300 mL). An emulsion formed in the ether layer, which was separable. The aqueous layer was extracted with ether (2×300 mL). The combined organic layers were filtered to remove emulsified material. The organic layer was washed with brine (200 mL), dried over sodium sulfate, filtered and evaporated to give 6.1 g (54%) of [1-(N-hydroxycarbamimidoyl)-spiro[2.5]oct-1-ylmethyl]-carbamic acid tert-butyl ester as a white solid: $^1$H NMR (300 MHz, CDCl$_3$) δ 0.52 (d, J=4.8 Hz, 1H), 0.90 (d, J=4.8 Hz, 1H), 1.4 (m, 1H), 1.43 (s, 9H), 1.3-1.7 (m, 9H), 3.11 (s, 1H), 3.23 (dd, J=5.2, 13.9 Hz, 1H), 3.47 (dd, J=5.2, 13.9 Hz, 1H), 4.68 (s, 2H), 5.12 (s, 1H); MS (APCI) m/z 298 [M+H]$^+$.

D. [1-(5-Oxo-4,5-dihydro-[1,2,4]oxadiazol-3-yl)-spiro[2.5]oct-1-ylmethyl]-carbamic acid tert-butyl ester To a solution of [1-(N-hydroxycarbamimidoyl)-spiro[2.5]oct-1-ylmethyl]-carbamic acid tert-butyl ester (5.8 g, 19.5 mmol) in THF (250 mL) was added CDI (4.74 g, 29.3 mmol). After 3 hours at reflux another portion of CDI (1 g) was added. The solution was heated to reflux for an additional 4 hours and then the solvent was removed under reduced pressure. The residue was partitioned between ether (200 mL) and 1N NaOH (75 mL). The organic layer was extracted with 1N NaOH (2×75 mL). The combined aqueous layers were washed with ether (100 mL). The aqueous layer was acidified to pH=3 by the addition of potassium hydrogen sulfate with ice bath cooling while layered over methylene chloride (100 mL). The layers were separated and the aqueous layer was extracted with methylene chloride (2×200 mL). The combined organic layers were washed with water (75 mL), dried over sodium sulfate, filtered and evaporated under reduced pressure to give an off white foam. The residue was chromatographed on a wet-packed silica gel column (6.5×28 cm) eluting with 3-4% methanol in methylene chloride. The appropriate fractions were combined and evaporated to give 4.4 g (70%) of [1-(5-oxo-4,5-dihydro-[1,2,4]oxadiazol-3-yl)-spiro[2.5]oct-1-ylmethyl]-carbamic acid tert-butyl ester as a white foam: $^1$H NMR (300 MHz, CDCl$_3$) δ0.78 (d, J=5.3 Hz, 1H), 1.44 (s, 9H), 1.3-1.7 (m, 11H), 3.24 (dd, J=5.0, 13.9 Hz, 1H), 3.84 (dd, J=5.0, 13.9 Hz, 1H), 4.97 (s, 1H); MS (APCI) m/z 324 [M+H]$^+$.

E. 3-(1-Aminomethyl-spiro[2.5]oct-1-yl)-4H-[1,2,4]oxadiazol-5-one hydrochloride

To a solution of [1-(5-oxo-4,5-dihydro-[1,2,4]oxadiazol-3-yl)-spiro[2.5]oct-1-ylmethyl]-carbamic acid tert-butyl ester (4.30 g, 13.3 mmol) in 1,4-dioxane (90 mL) was added 4N HCl in 1,4-dioxane (45 mL). The solution was stirred for 18 hours, ether (200 mL) was added and the precipitate isolated by vacuum filtration. The residue was chromatographed on a wet-packed silica gel column (5.5×30 cm) eluting with 80:20:5 CH$_2$Cl$_2$/MeOH/NH$_4$OH. The appropriate fractions were combined and evaporated under reduced pressure. The solid was stirred with 1N HCl in ether (150 mL). The solid was isolated by vacuum filtration, dried in a vacuum oven at 48° C. to give 2.22 g (64%) of 3-(1-aminomethyl-spiro[2.5]oct-1-yl)-4H-[1,2,4]oxadiazol-5-one hydrochloride as a white solid: mp: 179-181° C. (decomposition); $^1$H NMR (300 MHz, CD$_3$OD) δ 1.05 (d, J=5.8 Hz, 1H), 1.21 (m, 1H), 1.41 (d, J=5.8 Hz, 1H), 1.4-1.72 (m, 9H), 3.12 (d, J=14 Hz, 1H), 3.54 (d, J=14 Hz, 1H); MS (APCI) m/z 224 [M+H]$^+$. Anal. Calc'd For C$_{11}$H$_{17}$N$_3$O$_2$—HCl: C, 50.52; H, 7.01; N, 16.07; Cl, 13.56. Found: C, 50.23; H, 7.05; N, 15.89; Cl, 13.53.

Example 36

1-Aminomethyl-2-isopropyl-cyclopropanecarboxylic acid hydrochloride

A. 2-Cyano-4-methyl-pent-2-enoic acid methyl ester

To a solution of isobutyraldehyde (18.2 mL, 200 mmol) in dry benzene (20 mL) was added methyl cyanoacetate (18 mL, 200 mmol), ammonium acetate (2 g) and glacial acetic acid (4 mL). The reaction mixture was' stirred at 60° C. for 30 minutes and allowed to cool to room temperature. Excess of solvents was removed in vacuo and the residue was dissolved in EtOAc (200 mL). The organic layer was washed with water, dried over sodium sulfate and evaporated to give 2-cyano-4-methyl-pent-2-enoic acid methyl ester as pale yellow oil. Further purification of the pale yellow oil by distillation (7 mm Hg) gave product 2 (27.4 g, 56%) as colorless oil: $^1$H NMR (300 MHz, CDCl$_3$) δ 1.16 (d, J=6.6 Hz, 6H), 2.96-3.04 (m, 1H), 3.87 (s, 3H), 7.47 (d, J=10.5 Hz, 1H).

B. 1-Cyano-2-isopropyl-cyclopropanecarboxylic acid methyl ester

To a solution of 2-cyano-4-methyl-pent-2-enoic acid methyl ester (10.5 g, 68.3 mmol) in dry acetonitrile (60 mL) was added nitromethane (5.5 mL, 103 mmol) and a portionwise addition of alumina-supported potassium flouride (40% wt, 22 g). The reaction mixture was stirred under reflux for 2 hours and cooled to room temperature. The solid was removed by filtration through a short pad of celite and washed with acetonitrile. Excess of solvent was removed in vacuo and the residue was re-dissolved in ether. The ether layer was washed with water, brine, dried ($Na_2SO_4$) and concentrated in vacuo. The crude product was purified by flash column chromatography using hexanes/EtOAc (8:2) as an eluent to afford 1-cyano-2-isopropyl-cyclopropanecarboxylic acid methyl ester (7.7 g, 68%) as colorless oil: $^1$H NMR (300 MHz, $CDCl_3$) δ 1.13 (t, J=7.2 Hz, 6H), 1.39-1.45 (m, 2H), 1.65-1.74 (m, 1H), 1.81 (dd, J=4.4, 8.9 Hz, 1H), 3.81 (s, 3H); $^{13}$C NMR (75 MHz, $CDCl_3$) δ 19.6, 21.8, 21.9, 25.3, 31.2, 39.3, 53.7, 117.6, 168.7.

C. 1-(tert-Butoxycarbonylamino-methyl)-2-isopropyl-cyclopropanecarboxylic acid methyl ester To a solution of 1-cyano-2-isopropyl-cyclopropanecarboxylic acid methyl ester (7.7 g, 46.1 mmol) and cobaltous chloride hexahydrate (21.9 g, 92.2 mmol) in MeOH (560 mL) was added $NaBH_4$ (17.4 g, 461 mmol) in portions. The black precipitate formed was stirred for 1 hour at room temperature and was quenched with 0.5N HCl (200 mL). After the black precipitate dissolved, excess of solvent was removed and aqueous layer was made alkaline by addition of 2N NaOH. The alkaline solution was added slowly to a solution of di-tert-butyldicarbonate (20.1 g, 92.2 mmol) in dichloromethane (400 mL). The reaction mixture was stirred at room temperature overnight and the organic layer was separated and washed with brine and dried ($Na_2SO_4$). Evaporation of excess of solvent followed by purification of the residue by column chromatography using hexanes/EtOAc (9:1) as an eluent furnished 1-(tert-butoxycarbonylamino-methyl)-2-isopropyl-cyclopropanecarboxylic acid methyl ester (10.9 g, 88%) as colorless oil: $^1$H NMR (300 MHz, $CD_3OD$) δ 0.76 (m, 1H), 0.97 (d, J=6.3 Hz, 3H), 1.05 (d, J=6.3 Hz, 3H), 1.26-1.31 (m, 3H), 1.43 (s, 9H), 3.23 (d, J=14.3 Hz, 1H), 3.57 (d, J=14.3 Hz, 1H), 3.69 (s, 3H); $^{13}$C NMR (75 MHz, $CD_3OD$) δ 20.5, 23.4, 23.6, 29.2, 38.1, 41.1, 53.0, 80.5, 158.5, 177.1; MS (APCI) m/z 172 [M+H-100 (Boc)]$^+$.

D. 1-(tert-Butoxycarbonylamino-methyl)-2-isopropyl-cyclopropanecarboxylic acid

To a solution of 1-(tert-butoxycarbonylamino-methyl)-2-isopropyl-cyclopropanecarboxylic acid methyl ester (10.9 g, 40.2 mmol) in MeOH (320 mL) was added a solution of LiOH (4.2 g, 100 mmol) in water (98 mL). The reaction mixture was heated to reflux for 3 hours and cooled to room temperature. Excess of solvent was removed and the residue was dissolved in water (100 mL). The aqueous solution was washed with ether, acidified to pH=3 with 2N HCl and extracted with EtOAc (2×150 mL). The combined organic phase was washed with brine, dried ($Na_2SO_4$) and evaporation of the solvent provided 1-(tert-butoxycarbonylamino-methyl)-2-isopropyl-cyclopropanecarboxylic acid (9.0 g, 87%) as a colorless oil: $^1$H NMR (300 MHz, $CD_3OD$) δ 0.72 (m, 1H), 0.99 (d, J=6.2 Hz, 3H), 1.06 (d, J=6.2 Hz, 3H), 1.28-1.36 (m, 3H), 1.42 (s, 9H), 3.23 (d, J=14.3 Hz, 1H), 3.54 (d, J=14.3 Hz, 1H); $^{13}$C NMR (75 MHz, $CD_3OD$) δ 20.0, 23.0, 23.3, 28.8, 30.2, 37.6, 40.8, 80.2, 158.1, 178.5; MS (APCI) m/z 258 [M+H]$^+$.

E. 1-Aminomethyl-2-isopropyl-cyclopropanecarboxylic acid hydrochloride

To a solution of 1-(tert-butoxycarbonylamino-methyl)-2-isopropyl-cyclopropanecarboxylic acid (2.05 g, 8.0 mmol) in dry 1,4-dioxane (40 mL) was added 4N HCl (40 mL, in. 1,4-dioxane). The reaction mixture was stirred at room temperature overnight and ether was added (100 mL). The white solid was collected and dried to give 1-aminomethyl-2-isopropyl-cyclopropanecarboxylic acid hydrochloride (1.35 g, 88%): mp: 245-246° C.; $^1$H NMR (300 MHz, $D_2O$) δ 0.94 (d, J=6.5 Hz, 3H), 0.96 (m, 1H), 1.05 (d, J=6.4 Hz, 3H), 1.23-1.31 (m, 1H), 1.49-1.59 (m, 2H), 2.85 (d, J=13.7 Hz, 1H), 3.83 (d, J=13.7 Hz, 1H); $^{13}$C NMR (75 MHz, $D_2O$) δ 22.3, 23.9, 27.8, 30.8, 39.6, 41.7, 179.6; MS (APCI) m/z 158 [M+H]$^+$. Anal. Calc'd For $C_8H_{15}NO_2$—HCl: C, 49.61; H, 8.33; N, 7.23; Cl, 18.31. Found: C, 49.76; H, 8.44; N, 7.11; Cl, 18.48.

Example 37

1-Aminomethyl-2-isobutyl-cyclopropanecarboxylic acid hydrochloride

A. 2-Cyano-5 methyl-hex-2-enoic acid methyl ester

To a solution of isovaleraldehyde (86.1 g, 1 mol) in dry benzene (100 mL) was added methyl cyanoacetate 2 (99.1 g, 1 mol), ammonium acetate (10 g) and glacial acetic acid (20 mL). The reaction mixture was stirred at 0° C. for 1 hour and allowed to cool to room temperature. Excess of solvents was removed in vacuo and the residue was dissolved in EtOAc (400 mL). The organic layer was washed with water, dried over sodium sulfate and evaporated to give the product as pale yellow oil. Further purification of the pale yellow oil by distillation (10 mm Hg) gave 100 g (60%) of 2-cyano-5 methyl-hex-2-enoic acid methyl ester as a colorless oil: $^1$H NMR (300 MHz, $CDCl_3$) δ 1.00 (d, J=6.7 Hz, 6H), 1.91 (m, 1H), 2.47 (dd, J=7.9, 6.8 Hz, 2H), 3.89 (s, 3H), 7.69 (t, J=8.0 Hz, 1H).

B. 1-Cyano-2-isobutyl-cyclopropanecarboxylic acid methyl ester

To a solution of 2-cyano-5 methyl-hex-2-enoic acid methyl ester (20.2 g, 121 mmol) in dry acetonitrile (110 mL) was added nitromethane (9.8 mL, 181 mmol) and a portionwise addition of alumina-supported potassium flouride (40% wt, 39.3 g). The reaction mixture was stirred under reflux for 2 hours and cooled to room temperature. The solid was removed by filtration through a short pad of celite and washed with acetonitrile. Excess of solvent was removed in vacuo and the residue was re-dissolved in ether. The ether layer was washed with water, brine, dried ($Na_2SO_4$) and concentrated in vacuo. The crude product was purified by flash column chromatography using hexanes/EtOAc (8:2) as an eluent to give 15 g (69%) of 1-cyano-2-isobutyl-cyclopropanecarboxylic acid methyl ester as colorless oil: $^1$H NMR (300 MHz, $CDCl_3$) δ 0.98 (d, J=2.9 Hz, 3H), 1.00 (d, J=3.0 Hz, 3H), 1.35-1.42 (m, 2H), 1.65 (m, 1H), 1.79-1.94 (m, 3H), 3.81 (s, 3H); $^{13}$C NMR (75 MHz, $CDCl_3$) δ 19.3, 22.3, 22.4, 25.5, 27.9, 30.1, 39.0, 53.4, 117.3, 168.5.

C. 1-(tert-Butoxycarbonylamino-methyl)-2-isobutyl-cyclopropanecarboxylic acid methyl ester To a solution of 1-cyano-2-isobutyl-cyclopropanecarboxylic acid methyl ester (13.0 g, 71.8 mmol) and cobaltous chloride hexahydrate (34.2 g, 144 mmol) in MeOH (800 mL) was added $NaBH_4$ (27.2 g, 718 mmol) in portions. The black precipitate formed was stirred for 1 hour at room temperature and was quenched with 0.5N HCl (400 mL). After the black precipitate dissolved, excess of solvent was removed and aqueous layer was made alkaline by addition of 2N NaOH. The alkaline solution was added slowly to a solution of di-tert-butyldicarbonate (31.4 g, 144 mmol) in dichloromethane (600 mL). The reaction mixture was stirred at room temperature overnight and the organic layer was separated and washed with brine and dried ($Na_2SO_4$). Evaporation of excess of solvent followed by purification of the residue by column chromatography using hexanes/ EtOAc (9:1) as an eluent gave 16 g (78%) of 1-(tert-butoxycarbonylamino-methyl)-2-isobutyl-cyclopropanecarboxylic acid methyl ester as a colorless oil: $^1$H NMR (300 MHz, $CDCl_3$) δ 0.75 (m, 1H), 0.93 (t, J=6.5 Hz, 6H), 1.20-1.28 (m, 1H), 1.37 (dd, J=3.8, 8.5 Hz, 1H), 1.44 (s, 9H), 1.51-1.58 (m, 2H), 1.64-1.70 (m, 1H), 3.33-3.46 (m, 2H), 3.67 (s, 3H), 5.27 (m, 1H); $^{13}$C NMR (75 MHz, $CDCl_3$) δ 21.1, 22.4, 22.9, 26.7, 28.6, 28.7, 28.9, 37.8, 40.2, 52.1, 79.1, 156.1, 175.8; MS (APCI) m/z 186 [M+H-100(Boc)]$^+$.

D. 1-(tert-Butoxycarbonylamino-methyl)-2-isobutyl-cyclopropanecarboxylic acid

To a solution of 1-(tert-butoxycarbonylamino-methyl)-2-isobutyl-cyclopropanecarboxylic acid methyl ester (9.1 g, 31.9 mmol) in MeOH (260 mL) was added a solution of LiOH (3.34 g, 79.7 mmol) in water (80 mL). The reaction mixture was heated to reflux for 3 hours and cooled to room temperature. Excess of solvent was removed and the residue was dissolved in water (100 mL). The aqueous solution was washed with ether, acidified to pH=3 with 2N HCl and extracted with EtOAc (2×150 mL). The combined organic phase was washed with brine, dried ($Na_2SO_4$) and evaporation of the solvent gave 8.4 g (97%) of 1-(tert-butoxycarbonylamino-methyl)-2-isobutyl-cyclopropanecarboxylic acid as a colorless oil: $^1$H NMR (300 MHz, $CD_3OD$) δ 0.71 (dd, J=4.0, 6.4 Hz, 1H), 0.95 (t, J=6.4 Hz, 6H), 1.35 (m, 1H), 1.43 (s, 1H), 1.49-1.55 (m, 1H), 1.64-1.69-(m, 2H) 3.23 (d, J=14.2 Hz, 1H), 3.40 (d, J=14.2 Hz, 1H).

E. 1-Aminomethyl-2-isobutyl-cyclopropanecarboxylic acid hydrochloride

To a solution of 1-(tert-butoxycarbonylamino-methyl)-2-isobutyl-cyclopropanecarboxylic acid (2.8 g, 10.3 mmol) in dry 1,4-dioxane (60 mL) was added 4N HCl (40 mL, in 1,4-dioxane). The reaction mixture was stirred at room temperature overnight and ether was added (100 mL). The white solid was collected and dried to give 1.6 g (76%) of 1-aminomethyl-2-isobutyl-cyclopropanecarboxylic acid hydrochloride: mp: 254-255° C.; $^1$H NMR (300 MHz, $D_2O$) δ 0.95(t, J=6.2 Hz, 6H), 0.96 (m, 1H), 1.21-1.28 (m, 1H), 1.51-1.80 (m, 4H), 3.06 (d, J=13.8 Hz, 1H), 3.58 (d, J=13.8 Hz, 1H); $^{13}$C NMR (75 MHz, $D_2O$) δ 21.7, 21.9, 22.2, 25.3, 28.1, 28.6, 37.1, 40.2, 178.1; MS (APCI) m/z 172 [M+H]$^+$. Anal. Calc'd For $C_9H_{17}NO_2$—HCl: C, 52.05; H, 8.74; N, 6.74. Found: C, 52.10; H, 8.73; N, 6.67.

Example 38

3-(1-Aminomethyl-2-isopropyl-cyclopropyl)-4H-[1,2,4]oxadiazol-5-one hydrochloride A. (1-Carbamoyl-2-isopropyl-cyclopropylmethyl)-carbamic acid tert-butyl ester To a solution of 1-(tert-butoxycarbonylamino-methyl)-2-isopropyl-cyclopropanecarboxylic acid (6.4 g, 24.9 mmol) in dry THF (190 mL) was added HOBt (4.7 g, 34.8 mmol), NMM (3.83 mL, 34.8 mmol) and EDC (6.7 g, 34.8 mmol) at 0° C. The reaction mixture was stirred at 0° C. for 3 hours and quenched with concentrated ammonium hydroxide (16 mL). The reaction mixture was stirred at room temperature overnight. Excess of solvent was removed in vacuo and the residue was dissolved in EtOAc (200 mL). The organic layer was washed with 1N HCl, aqueous $NaHCO_3$, brine and dried over $Na_2SO_4$. Evaporation of excess of solvent gave 6.4 g (100%) of (1-carbamoyl-2-isopropyl-cyclopropylmethyl)-carbamic acid tert-butyl ester as a colorless oil: $^1$H NMR (300 MHz, $CD_3OD$) δ 0.62 (m, 1H), 1.00 (d, 3H), 1.05 (d, 3H), 1.25 (m, 3H), 1.45 (s, 9H), 3.05 (dd, 1H), 3.80 (dd, 1H), 6.70 (m, 1H); MS (APCI) m/z 257 [M+H]$^+$ B. (1-Cyano-2-isopropyl-cyclopropylmethyl)-carbamic acid tert-butyl ester To a solution of (1-carbamoyl-2-isopropyl-cyclopropylmethyl)-carbamic acid tert-butyl ester (6.4 g, 24.9 mmol) in dry DMF (100 mL) was added cyanuric chloride (6.4 g, 34.9 mmol). The reaction mixture was stirred at 0° C. for 30 minutes and was poured into cold 0.5N NaOH (200 mL). The aqueous phase was extracted with EtOAc (2×150 mL) and the combined organic layer was washed with water and brine and dried over $Na_2SO_4$. Removal of excess of solvent, followed by purification of the residue by flash column chromatography using hexanes/EtOAc (9:1) as eluent gave 4.4 g (74%) of (1-cyano-2-isopropyl-cyclopropylmethyl)-carbamic acid tert-butyl ester as a colorless foam: $^1$H NMR (300 MHz, $CDCl_3$) δ 0.87 (m, 1H), 1.05 (s, 6H), 1.23-1.33 (m, 3H), 1.45 (s, 9H), 3.29 (dd, J=6.3, 14.5 Hz, 1H), 3.47 (dd, J=6.1, 14.6 Hz, 1H), 5.31 (m, 1H); $^{13}$C NMR (75 MHz, $CDCl_3$) δ 14.6, 16.9, 21.0, 21.3, 27.1, 33.3, 39.3, 78.5, 122.0, 154.6; MS (APCI) m/z 239 [M+H]$^+$.

C. [1-(N-Hydroxycarbamimidoyl)-2-isopropyl-cyclopropylmethyl]-carbamic acid tert-butyl ester To a solution of (1-cyano-2-isopropyl-cyclopropylmethyl)-carbamic acid tert-butyl ester (4.4 g, 18.5 mmol) in ethanol (340 mL) was added hydroxylamine hydrochloride (6.4 g, 92.3 mmol) and finely powdered potassium hydroxide (5.18 g, 92.3 mmol). The reaction mixture was heated to reflux for 16 hours and cooled to room temperature. Excess of solvents was removed in vacuo and the residue was dissolved in ether/water mixture. The aqueous layer was extracted with ether (2×100 mL) and the combined ether extracts were washed with brine and dried over $Na_2SO_4$. Removal of excess of solvent in vacuo gave 5 g (100%) of [1-(N-hydroxycarbamimidoyl)-2-isopropyl-cyclopropylmethyl]-carbamic acid tert-butyl ester as colorless foam:

$^1$H NMR (300 MHz, $CD_3OD$) δ 0.45 (dd, J=5.5, 6.6 Hz, 1H), 0.88 (m, 1H), 1.04 (m, 7H), 1.35 (m, 1H), 1.41 (s, 9H), 3.15 (d, J=14.1 Hz, 1H), 3.53 (d, J=14.2 Hz, 1H); MS (ACPI) m/z272 [M+H]$^+$.

D. {2-Isopropyl-1-(5-oxo-4,5-dihydro-[1,2,4]oxadiazol-3-yl)-cyclopropylmethyl}-carbamic acid tert-butyl ester To a solution of [1-(N-hydroxycarbamimidoyl)-2-isopropyl-cyclopropylmethyl]-carbamic acid tert-butyl ester (5.0 g, 18.5 mmol) in dry THF (185 mL) was added dropwise a solution of carbonyl diimidazole (4.5 g, 27.8 mmol) in dry THF (185 mL). The reaction mixture was heated to reflux for 12 hours and allowed to cool to room temperature. Excess of solvents was removed in vacuo and the residue was partitioned between ether (100 mL) and 1N NaOH (100 mL) solution. The ethereal solution was extracted with 1N NaOH (2×50 mL) and the combined aqueous layers were acidified to pH=3 with 4N HCl solution. The aqueous solution was extracted with EtOAc (3×100 mL) and the combined organic phase was washed with brine and dried over Na$_2$SO$_4$. Removal of excess of solvent, followed by purification of the residue by flash column chromatography using hexanes/EtOAc (1:1) as an eluant gave 3.3 g (61%) of {2-isopropyl-1-(5-oxo-4,5-dihydro-[1,2,4]oxadiazol-3-yl)-cyclopropylmethyl}-carbamic acid tert-butyl ester as a colorless foam: $^1$H NMR (300 MHz, CD$_3$OD) δ 0.87 (dd, J=5.4, 6.8 Hz, 1H), 1.00 (m, 1H), 1.05 (d, J=5.2. Hz, 3H), 1.07 (d, J=5.1 Hz, 3H), 1.35 (m, 1H), 1.42 (s, 9H), 1.48 (m, 1H), 3.25 (d, J=14.7 Hz, 1H), 3.69 (d, J=14.7 Hz, 1H), 4.92 (s, 1H); $^{13}$C NMR (75 MHz, CD$_3$OD) δ 17.6, 23.2, 23.5, 24.7, 29.1, 30.3, 36.3, 41.3, 86.8, 158.7, 162.8, 164.4; MS (ACPI) m/z, 298 [M+H]$^+$.

E. 3-(1-Aminomethyl-2-isopropyl-cyclopropyl)-4H-[1,2,4]oxadiazol-5-one hydrochloride To a solution of {2-isopropyl-1-(5-oxo-4,5-dihydro-[1,2,4]oxadiazol-3-yl)-cyclopropylmethyl}-carbamic acid tert-butyl ester (3.30 g, 11.1 mmol) in dry 1,4-dioxane (20 ml) was added 4N HCl (40 mL, in 1,4-dioxane). The reaction mixture was stirred at room temperature overnight and diluted with ether (100 mL). The precipitate was collected and dried to give 1.6 g (62%) of 3-(1-aminomethyl-2-isopropyl-cyclopropyl)-4H-[1,2,4]oxadiazol-5-one hydrochloride as a white solid: mp: 178-179° C.; $^1$H NMR (300 MHz, D$_2$O) δ 1.01 (d, J=5.8 Hz, 3H), 1.10 (d, J=5.8 Hz, 3H), 1.22 (t, J=6.1 Hz, 1H), 1.38-1.46 (m, 2H), 1.56 (m, 1H), 3.12 (d, J=14.2 Hz, 1H), 3.93 (d, J=14.2 Hz, 1H); $^{13}$C NMR (75 MHz, D$_2$O) δ 18.1, 20.3, 21.7, 21.9, 29.0, 36.3, 39.3, 162.3, 162.5; MS (APCI) m/z 198 [M+H]$^+$. Anal. Calcd. For C$_9$H$_{15}$N$_3$O$_2$—HCl: C, 46.26; H, 6.90; N, 17.98; Cl, 15.17. Found: C, 46.39; H. 6.84; N, 17.85; Cl, 14.79.

Example 39

3-(1-Aminomethyl-2-isobutyl-cyclopropyl)-4H [1,2,4]oxadiazol-5-one hydrochloride A. (1-Carbamoyl-2-isobutyl-cyclopropylmethyl)-carbamic acid tert-butyl ester To a solution of 1-(tert-butoxycarbonylamino-methyl)-2-isobutyl-cyclopropanecarboxylic acid (5.2 g, 19.2 mmol) in dry THF (190 mL) was added HOBt (2.85 g, 21.1 mmol), NMM (2.32 mL, 21.1 mmol) and EDC (4.0 g, 21.1 mmol) at 0° C. The reaction mixture was stirred at 0° C. for 3 hours and quenched with concentrated ammonium hydroxide (16 mL). The reaction mixture was stirred at room temperature overnight. Excess of solvent was removed in vacuo and the residue was dissolved in EtOAc (200 mL). The organic layer was washed with 1N HCl, aqueous NaHCO$_3$, brine and dried over Na$_2$SO$_4$. Evaporation of excess of solvent gave 3.5 g (69%) of (1-carbamoyl-2-isobutyl-cyclopropylmethyl)-carbamic acid tert-butyl ester as a colorless oil: $^1$H NMR (300 MHz, CD$_3$OD) & 0.61 (dd, J=4.2, 6.5 Hz, 1H), 0.94 (d, J=5.0 Hz, 3H), 0.96 (d, J=5.0 Hz, 3H), 1.20 (m, 1H), 1.29 (dd, J=3.9, 8.7 Hz, 1H), 1.44 (s, 9H), 1.51 (m, 2H), 1.65 (m, 1H), 3.20 (d, J=15.2 Hz, 1H), 3.54 (d, J=15.2 Hz, 1H); $^{13}$C (75 MHz, CD$_3$OD) δ 21.5, 23.2, 23.6, 27.4, 29.3, 30.3, 30.4, 39.3, 41.8, 80.9, 159.3, 179.9; MS (APCI) m/z 271 [M+H]$^+$.

B. (1-Cyano-2-isobutyl-cyclopropylmethyl)-carbamic acid tert-butyl ester

To a solution of (1-carbamoyl-2-isobutyl-cyclopropylmethyl)-carbamic acid tert-butyl ester (5.8 g, 21.5 mmol) in dry DMF (100 mL) was added cyanuric chloride (5.5 g, 30.1 mmol). The reaction mixture was stirred at 0° C. for 30 minutes and was poured into cold 0.5N NaOH (200 mL). The aqueous phase was extracted with EtOAc (2×150 mL) and the combined organic layer was washed with water and brine and dried over Na$_2$SO$_4$. Removal of excess of solvent, followed by purification of the residue by flash column chromatography using hexanes/EtOAc (9:1) as eluent gave 4.9 g (91%) of (1-cyano-2-isobutyl-cyclopropylmethyl)-carbamic acid tert-butyl ester as a colorless foam: $^1$H NMR (300 MHz, CDCl$_3$) δ 0.86 (m, 1H), 0.94 (d, J=4.0 Hz, 3H), 0.96 (d, J=4.0 Hz, 3H), 1.56 (m, 1H), 1.37-1.56 (m, 12H), 1.71 (m, 1H), 3.32 (d, J=6.1 Hz, 2H), 5.26 (s, 1H); $^{13}$C (75 MHz, CDCl$_3$) δ 14.5, 18.8, 21.9, 22.2, 24.4, 28.0, 28.1, 36.3, 40.4, 79.3, 122.9, 155.4; MS (APCI) m/z 253 [M+H]$^+$.

C. [1-(N-Hydroxycarbamimidoyl)-2-isobutyl-cyclopropylmethyl]-carbamic acid tert-butyl ester To a solution of (1-cyano-2-isobutyl-cyclopropylmethyl)-carbamic acid tert-butyl ester (4.9 g, 19.4 mmol) in ethanol (360 mL) was added hydroxylamine hydrochloride (6.8 g, 97.1 mmol) and finely powdered potassium hydroxide (5.45 g, 97.1 mmol). The reaction mixture was heated to reflux for 16 hours and cooled to room temperature. Excess of solvents was removed in vacuo and the residue was dissolved in ether/water mixture. The aqueous layer was extracted with ether (2×100 mL) and the combined ether extracts were washed with brine and dried over Na$_2$SO$_4$. Removal of excess of solvent in vacuo gave 5.6 g (100%) of [1-(N-hydroxycarbamimidoyl)-2-isobutyl-cyclopropylmethyl]-carbamic acid tert-butyl ester as a colorless foam:

$^1$H NMR (300 MHz, CD$_3$OD) δ 0.44 (t, J=4.4 Hz, 1H), 0.95 (t, J=5.5 Hz, 6H), 1.09-1.23 (m, 3H), 1.42 (s, 9H), 1.63-1.70 (m, 2H), 3.25 (d, J=14.3 Hz, 1H), 3.33 (d, J=14.3 Hz, 1H), 4.93 (bs, 3H); MS (APCI) m/z 286 [M+H]$^+$.

D. {2-Isobutyl-1-(5-oxo-4,5-dihydro-[1,2,4]oxadiazol-3-yl)-cyclopropylmethyl}-carbamic acid tert-butyl ester To a solution of [1-(N-hydroxycarbamimidoyl)-2-isobutyl-cyclopropylmethyl]-carbamic acid tert-butyl ester (5.6 g, 19.6 mmol) in dry THF (190 mL) was added dropwise a solution of carbonyl diimidazole (4.8 g, 29.4 mmol) in dry THF (190 mL). The reaction mixture was heated to reflux for 12 hours and allowed to cool to room temperature. Excess of solvents was removed in vacuo and the residue was partitioned between ether (100 mL) and 1N NaOH (100 mL) solution. The ethereal solution was extracted with 1N NaOH (2×50 mL) and the combined aqueous layers were acidified to pH=3 with 4N HCl solution. The aqueous solution was extracted with EtOAc (3×100 mL) and the combined organic phase was washed with brine and dried over Na$_2$SO$_4$. Removal of excess of solvent, followed by purification of the residue by flash column chromatography using hexanes/EtOAc (1:1) as an eluent gave 4.66 g (76%) of {2-isobutyl-1-(5-oxo-4,5-dihydro-[1,2,4]oxadiazol-3-yl)-cyclopropylmethyl}-carbamic acid tert-butyl ester as a colorless foam: $^1$H NMR (300 MHz, CD$_3$OD) δ 0.89 (t, J=5.7 Hz, 1H), 0.96 (d, J=5.1 Hz, 3H), 0.98 (d, J=5.1 Hz, 3H), 1.26-1.37 (m, 3H), 1.43 (s, 9H), 1.63-1.71 (m, 2H), 3.35 (d, J=14.8 Hz, 1H), 3.53 (d, J=14.8 Hz, 1H); MS (APCI) m/z 210 [M+H-100(Boc)]$^+$.

E. 3-(1-Aminomethyl-2-isobutyl-cyclopropyl)-4H-[1,2,4]oxadiazol-5-one hydrochloride To a solution of {2-isobutyl-1-(5-oxo-4,5-dihydro-[1,2,4]oxadiazol-3-yl)-cyclopropylmethyl}-carbamic acid tert-butyl ester (4.2 g, 13.5 mmol) in dry 1,4-dioxane (20 ml) was added 4N HCl (40 mL, in 1,4-dioxane). The reaction mixture was stirred at room temperature overnight and diluted with ether (100 mL). The precipitate was collected and washed with ether and dried to give 2.6 g (79%) of 3-(1- aminomethyl-2-isobutyl-cyclopropyl)-4H-[1,2,4]oxadiazol-5-one hydrochloride as a white solid: mp: 181-182° C.; $^1$H NMR (300 MHz, D$_2$O) δ 0.94-0.98 (m, 6H), 1.21 (m, 1H), 1.35 (m, 1H), 1.58 (m, 3H), 1.73 (m, 1H), 3.24 (d, J=14.2 Hz, 1H), 3.71 (d, J=14.3 Hz, 1H); $^{13}$C NMR (75 MHz, D$_2$O) δ 19.3, 19.6, 21.8, 22.1, 26.6, 28.2, 36.7, 39.5, 162.2, 162.6; MS (APCI) m/z 212 [M+H]$^+$. Anal. Calc'd For C$_{10}$H$_{17}$N$_3$O$_2$—HCl: C, 48.49; H, 7.32; N, 16.96; Cl, 14.31. Found: C, 48.49; H, 7.17; N, 16.84; Cl, 13.94.

What is claimed is:

1. A compound of the formula

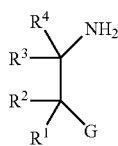

wherein G is

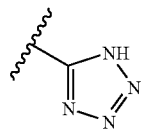

wherein R$^1$ is selected from (C$_2$-C$_{10}$)straight or branched alkyl, (C$_1$-C$_{10}$)straight or branched alkyl substituted with (C$_3$-C$_8$)cycloalkyl, (C$_2$-C$_{10}$)straight or branched alkoxy-alkyl, (C$_3$-C$_8$)cycloalkyl optionally substituted with one or two (C$_1$-C$_3$)alkyl substituents, phenyl-(C$_1$-C$_4$)straight or branched alkyl and phenyl-(C$_2$-C$_3$) alkoxyalkyl, wherein said phenyl moieties can optionally be substituted with one or two substituents selected, independently, from halo, CF$_3$ or (C$_1$-C$_4$)alkyl;

R$^2$ is hydrogen;

or R$^1$ and R$^2$, together with the carbon to which they are attached, form a cyclopentyl, cyclohexyl or cycloheptyl ring which can optionally be substituted with one or two substituents selected, independently, from the group of substituents named in the definition of R$^1$ and R$^2$ above; and R$^3$ and R$^4$ are hydrogen;

or a pharmaceutically acceptable salt thereof.

2. The compound according to claim 1, selected from the following compounds, or a pharmaceutically acceptable salt thereof:

4-Methyl-2-(1H-tetrazol-5-yl)-pentylamine;
3-Methyl-2-(1H-tetrazol-5-yl)-butylamine;
4-Propyl-2-(1H-tetrazol-5-yl)-heptylamine;
2-Cyclopentyl-2-(1H-tetrazol-5-yl)-ethylamine;
4-Methyl-2-(1H-tetrazol-5-yl)-hexylamine;
4,4-Dimethyl-2-(1H-tetrazol-5-yl)-hexylamine;
4-Ethyl-2-(1H-tetrazol-5-yl)-hexylamine;
4-Ethyl-2-(1H-tetrazol-5-yl)-octylamine;
4,4-Dimethyl-2-(1H-tetrazol-5-yl)-heptylamine;
5,5-Dimethyl-2-(1H-tetrazol-5-yl)-hexylamine;
2-(1H-Tetrazol-5-yl)-pentylamine;
2-(1H-Tetrazol-5-yl)-octylamine;
4,8-Dimethyl-2-(1H-tetrazol-5-yl)-nonylamine;
5,9-Dimethyl-2-(1H-tetrazol-5-yl)-decylamine;
2-Cyclohexyl-2-(1H-tetrazol-5-yl)-ethylamine;
2-(3,5-Dimethyl-cyclohexyl)-2-(1H-tetrazol-5-yl)-ethylamine;
2-Cycloheptyl-2-(1H-tetrazol-5-yl)-ethylamine;
3-Cyclohexyl-2-(1H-tetrazol-5-yl)-propylamine;
3,4-Dimethyl-2-(1H-tetrazol-5-yl)-pentylamine;
3-Ethyl-4-methyl-2-(1H-tetrazol-5-yl)-pentylamine;
4-Cyclopentyl-3-methyl-2-(1H-tetrazol-5-yl)-butylamine;
4-Cyclohexyl-3-methyl-2-(1H-tetrazol-5-yl)-butylamine;
4-(4-Fluoro-phenyl)-3-methyl-2-(1H-tetrazol-5-yl)-butylamine;
3-Methyl-2-(1H-tetrazol-5-yl)-4-(3-trifluoromethyl-phenyl)-butylamine;
3-Methyl-5-phenyl-2-(1H-tetrazol-5-yl)-pentylamine;
5-(4-tert-Butyl-phenyl)-4-methyl-2-(1H-tetrazol-5-yl)-pentylamine;
2-Methyl-2-(1H-tetrazol-5-yl)-propylamine; and
2-Methyl-3-phenyl-2-(1H-tetrazol-5-yl)-propylamine.

3. A pharmaceutical composition comprising a compound or salt according to claim 1, and a pharmaceutically acceptable carrier.

4. A method of treating epilepsy in a mammal, comprising administering to a mammal in need of such treatment a therapeutically effective amount of a compound or salt according to claim 1.

5. A method of treating chronic pain selected from diabetic neuropathy and neuropathic lower back pain in a mammal, comprising administering to a mammal in need of such treatment a therapeutically effective amount of a compound or salt according to claim 1.

6. A method of treating an anxiety disorder or condition selected from childhood anxiety disorder, panic disorder with or without agoraphobia, agoraphobia without history of panic disorder, social anxiety disorder, social phobia and obsessive-compulsive disorder, in a mammal, comprising administering to a mammal in need of such treatment a therapeutically effective amount of a compound or salt according to claim 1.

7. The compound or salt according to claim 1, wherein R$^1$ is (C$_2$-C$_{10}$)straight or branched alkyl, (C$_1$-C$_{10}$)straight or branched alkyl substituted with (C$_3$-C$_8$)cycloalkyl, or (C$_3$-C$_8$)cycloalkyl optionally substituted with one or two (C$_1$-C$_3$)alkyl substituents.

* * * * *